United States Patent
Nagasawa

(10) Patent No.: US 12,165,762 B2
(45) Date of Patent: Dec. 10, 2024

(54) DELIVERY MANAGEMENT SYSTEM

(71) Applicant: MEDIPAL HOLDINGS CORPORATION, Tokyo (JP)

(72) Inventor: Kazunori Nagasawa, Tokyo (JP)

(73) Assignee: MEDIPAL HOLDINGS CORPORATION, Tokyo (JP)

( * ) Notice: Subject to any disclaimer, the term of this patent is extended or adjusted under 35 U.S.C. 154(b) by 268 days.

(21) Appl. No.: 17/756,177

(22) PCT Filed: Nov. 22, 2019

(86) PCT No.: PCT/JP2019/045841
§ 371 (c)(1),
(2) Date: May 18, 2022

(87) PCT Pub. No.: WO2021/100203
PCT Pub. Date: May 27, 2021

(65) Prior Publication Data
US 2023/0005604 A1     Jan. 5, 2023

(51) Int. Cl.
*G16H 40/20*       (2018.01)
*G06Q 10/0832*    (2023.01)

(52) U.S. Cl.
CPC ......... *G16H 40/20* (2018.01); *G06Q 10/0832* (2013.01)

(58) Field of Classification Search
None
See application file for complete search history.

(56) References Cited

U.S. PATENT DOCUMENTS

2009/0289448 A1* 11/2009 Sample ............... B01L 3/5457
                                                                  283/67
2015/0039342 A1*  2/2015 Chen .................... G16H 10/40
                                                                  705/3

FOREIGN PATENT DOCUMENTS

| JP | 2008-249359 A | 10/2008 |
| JP | 2014-052741 A |  3/2014 |
| JP | 2018-004619 A |  1/2018 |
| JP | 2018-195278 A | 12/2018 |

OTHER PUBLICATIONS

WIPO, Japan International Search Authority, International Search Report and Written Opinion mailed Feb. 18, 2020 in International Patent Application No. PCT/JP2019/045841, 10 pages.

* cited by examiner

*Primary Examiner* — Devin C Hein
(74) *Attorney, Agent, or Firm* — MASUVALLEY & PARTE; Peter Martinez

(57) ABSTRACT

A delivery management system includes a drug wrapping 140, a delivery container 26, a delivery management device 7, and a barcode sheet 137. The barcode sheet 137 includes a barcode label 137c indicating a serial number related to a drug, a barcode-image portion 137e indicating the serial number related to the drug, and a barcode label 137d indicating a delivery-container ID related to the delivery container. When the drug wrapping to which the barcode label 137c separated from the barcode sheet is attached, the delivery container, and the barcode sheet from which the barcode label 137c has been separated reach a delivery destination, the drug wrapping is verified using the barcode label 137d attached to the delivery container and the barcode-image portion 137e.

7 Claims, 19 Drawing Sheets

[HARDWARE CONFIGURATION DIAGRAM OF DELIVERY CONTAINER]

[HARDWARE CONFIGURATION DIAGRAM OF PDA TERMINAL]

[HARDWARE CONFIGURATION DIAGRAM OF WAREHOUSE TERMINAL]

FIG.6
[DIAGRAM CORRESPONDING TO CLAIMS]
(a)
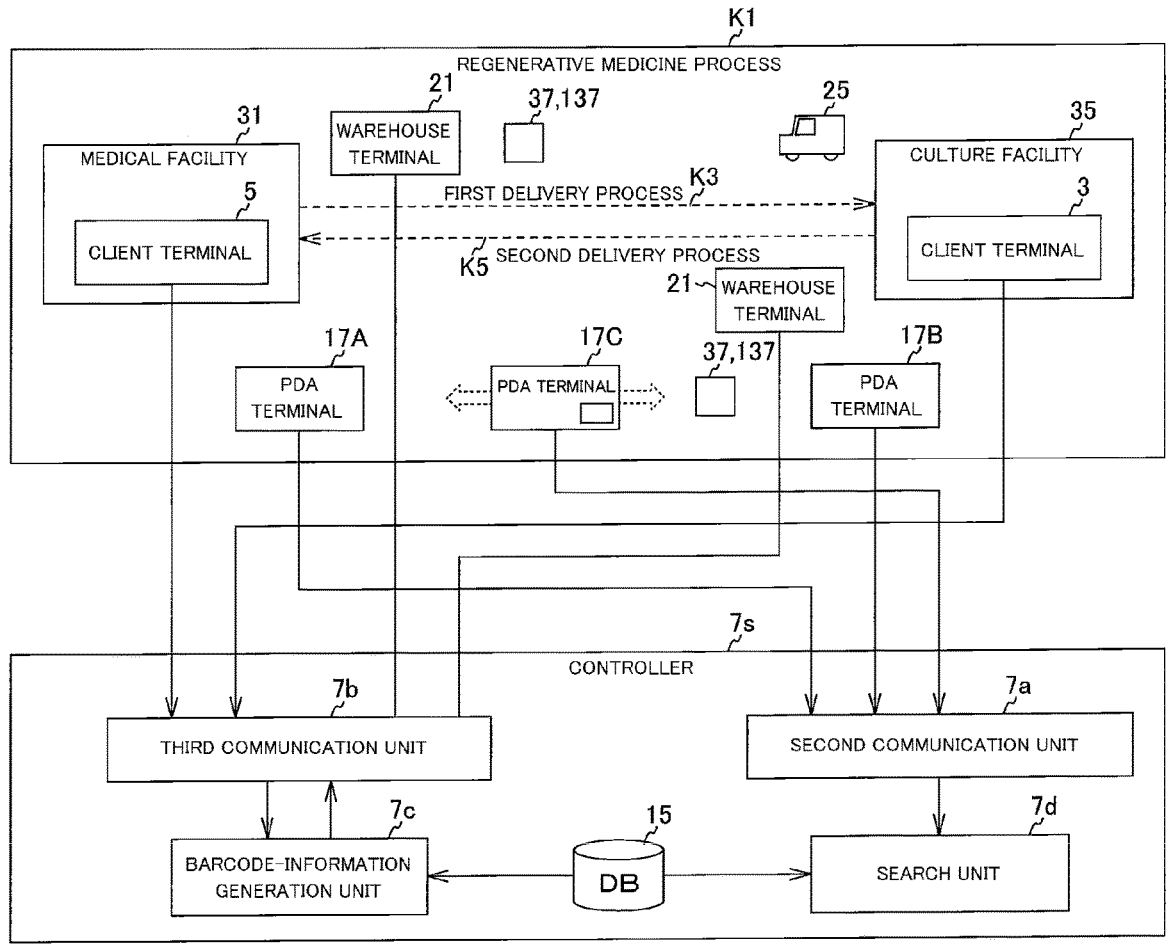
(b)
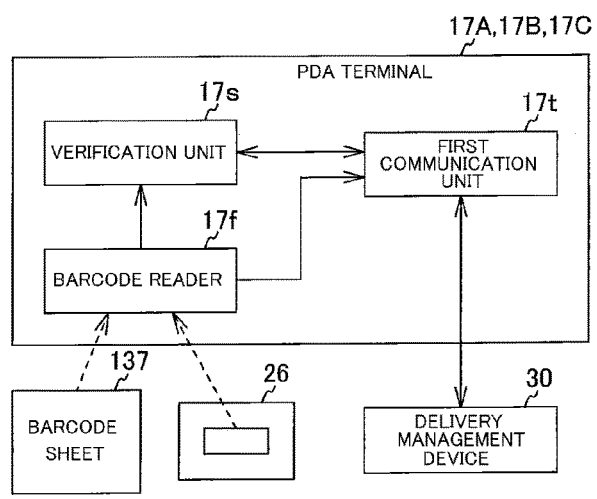

FIG.11

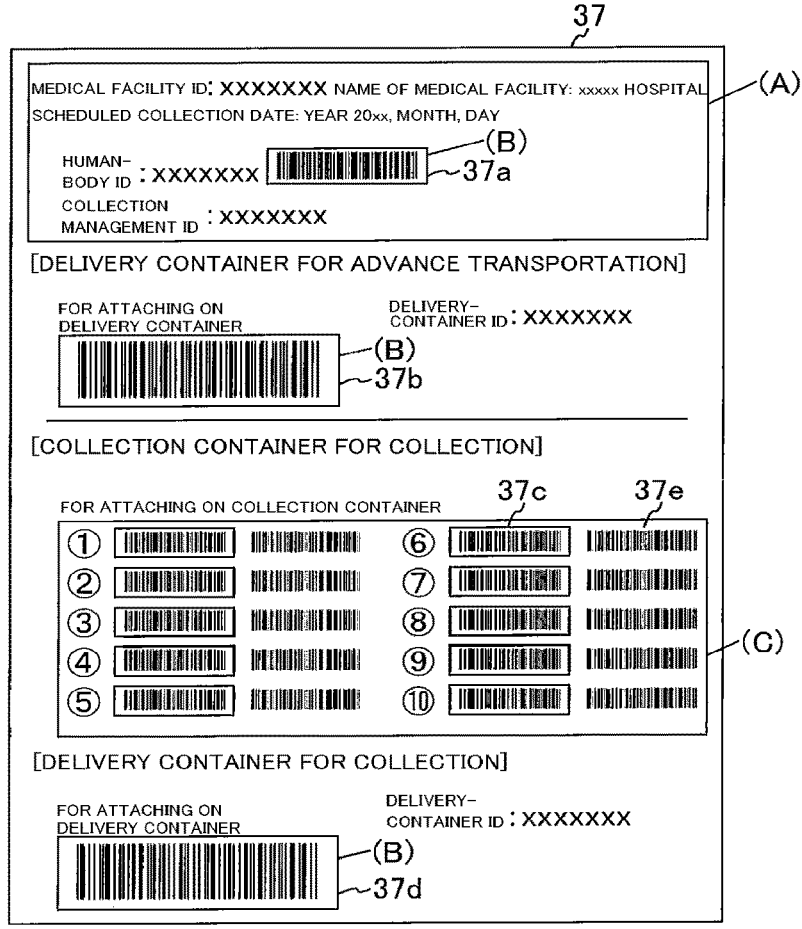

FIG.12

LIST OF OUTPUT SOURCE OF BARCODE SHEET DATA

| | |
|---|---|
| MEDICAL FACILITY ID | MEDICAL FACILITY M. MEDICAL FACILITY CODE |
| NAME OF MEDICAL FACILITY | MEDICAL FACILITY M. MEDICAL FACILITY NAME |
| SCHEDULED COLLECTION DATE | COLLECTION-CONTAINER STATUS F. COLLECTION DATE |
| HUMAN-BODY ID | HUMAN-BODY MANAGEMENT F. HUMAN-BODY ID |
| HUMAN-BODY ID BARCODE | HUMAN-BODY MANAGEMENT F. HUMAN-BODY ID |
| COLLECTION MANAGEMENT ID | COLLECTION MANAGEMENT F. COLLECTION MANAGEMENT ID |
| [DELIVERY CONTAINER FOR ADVANCE TRANSPORTATION] DELIVERY CONTAINER ID | COLLECTION MANAGEMENT F. DELIVERY-CONTAINER ID |
| [DELIVERY CONTAINER FOR ADVANCE TRANSPORTATION] CONTAINER IDENTIFICATION BARCODE | COLLECTION MANAGEMENT F. DELIVERY-CONTAINER ID + COLLECTION MANAGEMENT F. COLLECTION MANAGEMENT ID + STATUS (ADVANCE DELIVERY) |
| [COLLECTION CONTAINER FOR COLLECTION] BARCODE | COLLECTION MANAGEMENT F. COLLECTION-CONTAINER ID (n) |
| [DELIVERY CONTAINER FOR COLLECTION] DELIVERY CONTAINER ID | COLLECTION MANAGEMENT F. DELIVERY-CONTAINER ID |
| [DELIVERY CONTAINER FOR COLLECTION] CONTAINER IDENTIFICATION BARCODE | COLLECTION MANAGEMENT F. DELIVERY-CONTAINER ID + COLLECTION MANAGEMENT F. COLLECTION MANAGEMENT ID + STATUS (COLLECTION) |

FIG.19

LIST OF OUTPUT SOURCE OF BARCODE SHEET DATA

| | |
|---|---|
| MEDICAL FACILITY ID | MEDICAL FACILITY M. MEDICAL FACILITY CODE |
| NAME OF MEDICAL FACILITY | MEDICAL FACILITY M. MEDICAL FACILITY NAME |
| SCHEDULED ADMINISTRATION DATE | DRUG STATUS F. ADMINISTRATION DATE |
| HUMAN-BODY ID | HUMAN-BODY MANAGEMENT F. HUMAN-BODY ID |
| HUMAN-BODY ID BARCODE | HUMAN-BODY MANAGEMENT F. HUMAN-BODY ID |
| ADMINISTRATION MANAGEMENT ID | ADMINISTRATION MANAGEMENT F. ADMINISTRATION MANAGEMENT ID |
| DRUG ID | ADMINISTRATION MANAGEMENT F. DRUG ID |
| [DELIVERY CONTAINER FOR ADVANCE TRANSPORTATION] DELIVERY-CONTAINER ID | ADMINISTRATION MANAGEMENT F. DELIVERY-CONTAINER ID |
| [DELIVERY CONTAINER FOR ADVANCE TRANSPORTATION] CONTAINER IDENTIFICATION BARCODE | ADMINISTRATION MANAGEMENT F. DELIVERY CONTAINER ID<br>+ ADMINISTRATION MANAGEMENT F. ADMINISTRATION MANAGEMENT ID<br>+ ADMINISTRATION MANAGEMENT F. DRUG ID<br>+ STATUS (ADVANCE DELIVERY) |
| [DRUG FOR ACCOMMODATION] BARCODE | ADMINISTRATION MANAGEMENT F. SERIAL NUMBER (n) |
| [DELIVERY CONTAINER FOR ACCOMMODATION] DELIVERY CONTAINER ID | ACCOMMODATION MANAGEMENT F. DELIVERY CONTAINER ID |
| [DELIVERY CONTAINER FOR ACCOMMODATION] CONTAINER IDENTIFICATION BARCODE | ACCOMMODATION MANAGEMENT F. DELIVERY-CONTAINER ID<br>+ ACCOMMODATION MANAGEMENT F. ACCOMMODATION MANAGEMENT ID<br>+ ACCOMMODATION MANAGEMENT F. DRUG ID<br>+ STATUS (COLLECTION) |

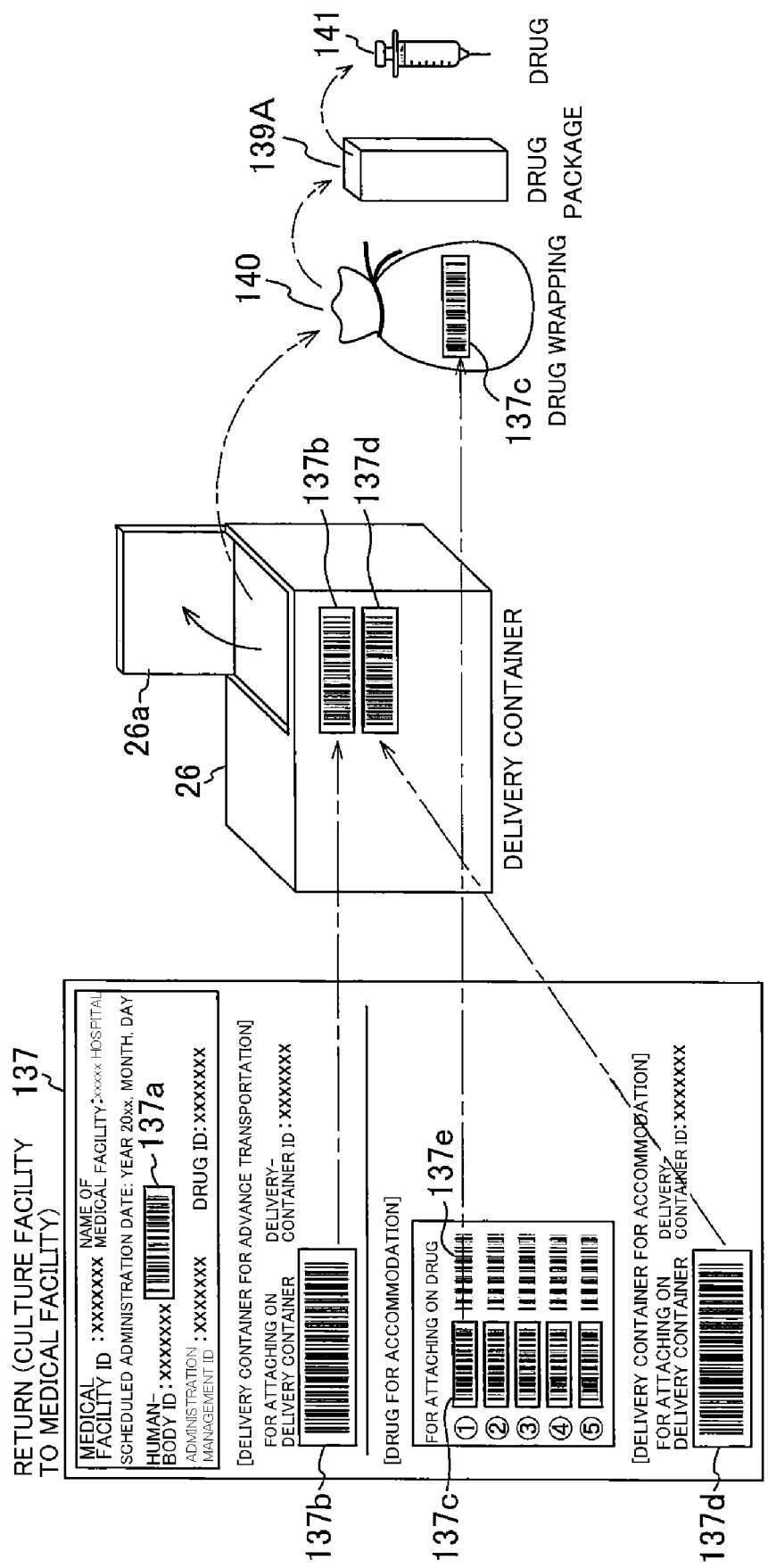

DELIVERY MANAGEMENT SYSTEM

RELATED APPLICATIONS

This application is the U.S. National Phase of and claims priority to International Patent Application No. PCT/JP2019/045851, International Filing Date Nov. 22, 2019, entitled Delivery Management System; which is incorporated herein by reference in its entirety.

FIELD

The present invention relates to a delivery management system for generating barcode information related to barcode labels to be used for delivering a collected material collected from the body of a patient in a medical facility to a culture facility or delivering a drug cultured from the collected material in the culture facility to the medical facility for a regenerative medicine process related to autologous cells.

BACKGROUND

In recent years, autologous cell transplantation has been performed in which cells collected from the body of a patient are cultured, a drug is generated, and the drug is transplanted into the body of the patient. In order to perform this autologous cell transplantation, a cell culture center (hereinafter, "culture facility") in which the collected cells are expertly cultured is required.

In autologous cell transplantation, different dedicated containers have to be used as a first container used exclusively for delivering cells collected from the body of a patient in a medical facility to a culture facility and a second container used exclusively for delivering a drug cultured in the culture facility to the medical facility where the patient is present, because the first and the second containers are different in storage capacity, storage temperature, storage humidity, and the like.

In a conventional medical facility, the name of a patient is described in order to specify the patient and the pathological material. For example, in a case where the pathological material is a biopsy specimen, the pathological material is collected in an endoscopy room or the like and carried to a pathology laboratory. Therefore, the name of the patient displayed on a pathological-material container is copied to an endoscopy-room nursing record or a pathological request document created in the endoscopy room in order to manage the pathological material. Further, in the pathology laboratory, the name of the patient described on the pathological-material container is copied to pathological-material reception records, an issued pathological number ledger, or the like.

Since the name of the patient described on the pathological-material container is copied to the endoscopy-room nursing record, the pathological request document, the pathological-material reception records, the issued pathological number ledger, or the like as described above, mix-up of patients or mix-up of pathological materials may occur because of a copying error.

In order to provide a pathological-material container that can prevent mix-up of patients or pathological materials and can surely manage a pathological material collected from a patient, Patent Literature 1 discloses a technique characterized by including a container body in which a fixative for fixing a pathological material collected from a patient is accommodated, a lid for sealing the container body, and a multi-label including a plurality of labels that are connected to each other in a disconnectable manner and indicate the same container serial number. One of the labels is attached to the lid, and the remaining labels are attached to the container body.

In Patent Literature 1, one of the labels indicating the same container serial number is attached to the lid, and the remaining labels are attached to the container body. A person who carries a biopsy specimen collected in the endoscopy room carries the pathological-material container and a pathological request document from the endoscopy room to the pathology laboratory for pathological examination. A pathologist assistant in the pathology laboratory confirms that the biopsy specimen is present in the carried pathological-material container, and confirms that the container serial numbers of the label attached to the pathological-material container and the label attached to the pathology request document match each other.

CITATION LIST

Patent Literature

Patent Literature 1: Japanese Patent Application Laid-open No. 2018-4619

SUMMARY

Technical Problem

However, in a case of diverting the invention described in Patent Literature 1 to the above-described regenerative medicine process related to autologous cells, the following problems arise.

(1) In Patent Literature 1, the pathologist assistant visually confirms that the container serial numbers of the label attached to the pathological-material container and the label attached to the pathology request document match each other, and therefore a work burden is imposed on the pathologist assistant. However, when such a technique based on visual confirmation by human is diverted to a delivery system of a delivery company that delivers a large number of articles, there arises a problem that a large work burden is imposed on a delivery person of the delivery company.

(2) Patent Literature 1 discloses a technique in which a barcode reader connected to a terminal constituting a pathology subsystem is used to read a two-dimensional barcode of the label attached to the pathological-material container and to input the container serial number. However, there is no disclosure of how the pathology subsystem performs the confirmation process.

(3) Patent Literature 1 discloses that the pathological material collected from a patient is accommodated in a pathological-material container and carried from the endoscopy room to the pathology laboratory in the same medical facility.

However, there is no description that delivery of the pathological-material container is requested to the delivery company, and the container is delivered while being accommodated in a larger carrying container. Further, Patent Literature 1 fails to disclose mix-up of carrying containers each accommodating therein such a pathological-material container.

(4) For example, when the pathological-material container is kept warm at a predetermined temperature, the pathological-material container needs to be accommodated in a heat insulating container larger than the pathological-material container. Therefore, in order to acquire the container serial number from the label attached to the pathological-material container, the heat insulating container needs to be opened once, which results in temporal temperature rise during heat insulation and exposes the pathological-material container to a dangerous situation.

Therefore, for a regenerative medicine process related to autologous cells, in which a collected material collected from the body of a patient in a medical facility is delivered to a culture facility and a drug cultured from the collected material in the culture facility is delivered to the medical facility, there are demands for preventing mix-up of a plurality of different kinds of delivered articles including, for example, a collection container accommodating therein the collected material, a drug package accommodating therein the drug, and a delivery container accommodating therein the collection container or the drug package and for automating a verification process.

An embodiment of the present invention has been made in view of the above problems, and an object of the embodiment is to prevent mix-up of a plurality of different kinds of delivered articles without opening a delivery container and to automate a verification process, for a regenerative medicine process.

Solution to Problem

In order to solve the above problems, the invention according to claim 1 comprises: an article container for accommodating therein an article; a delivery container for accommodating therein the article container and delivering the article container; a delivery management device that generates barcode image data specifying each of the article container and the delivery container; and a barcode sheet on which a barcode image is printed based on the barcode image data generated by the delivery management device, wherein the barcode sheet includes a first barcode label indicating a serial number related to the article, a barcode-image portion indicating the serial number related to the article, and a second barcode label indicating a delivery-container ID related to the delivery container, and when an article container to which the first barcode label separated from the barcode sheet is attached, the delivery container, and the barcode sheet from which the first barcode label has been separated reach a delivery destination, the article container is verified using the second barcode label attached to the delivery container and the barcode-image portion at the delivery destination.

Advantageous Effects of Invention

According to the present invention, it is possible to prevent mix-up of a plurality of different kinds of delivered articles without opening a delivery container and automate a verification process for a regenerative medicine process.

BRIEF DESCRIPTION OF DRAWINGS

FIG. 6(a) is a functional block diagram of the delivery management system according to the first embodiment of the present invention, and FIG. 6(b) is a functional block diagram of the PDA terminal according to the first embodiment of the present invention.

FIG. 11 is a diagram illustrating overview of a barcode sheet according to the first embodiment of the present invention.

FIG. 12 is a diagram illustrating a list of data output source of the barcode sheet according to the first embodiment of the present invention.

FIG. 19 is a diagram illustrating a list of data output source of the barcode sheet according to the second embodiment of the present invention.

FIG. 20 is a schematic diagram illustrating a barcode label according to the second embodiment of the present invention and a container to which the barcode label is attached.

DESCRIPTION OF EMBODIMENTS

Figure 1:
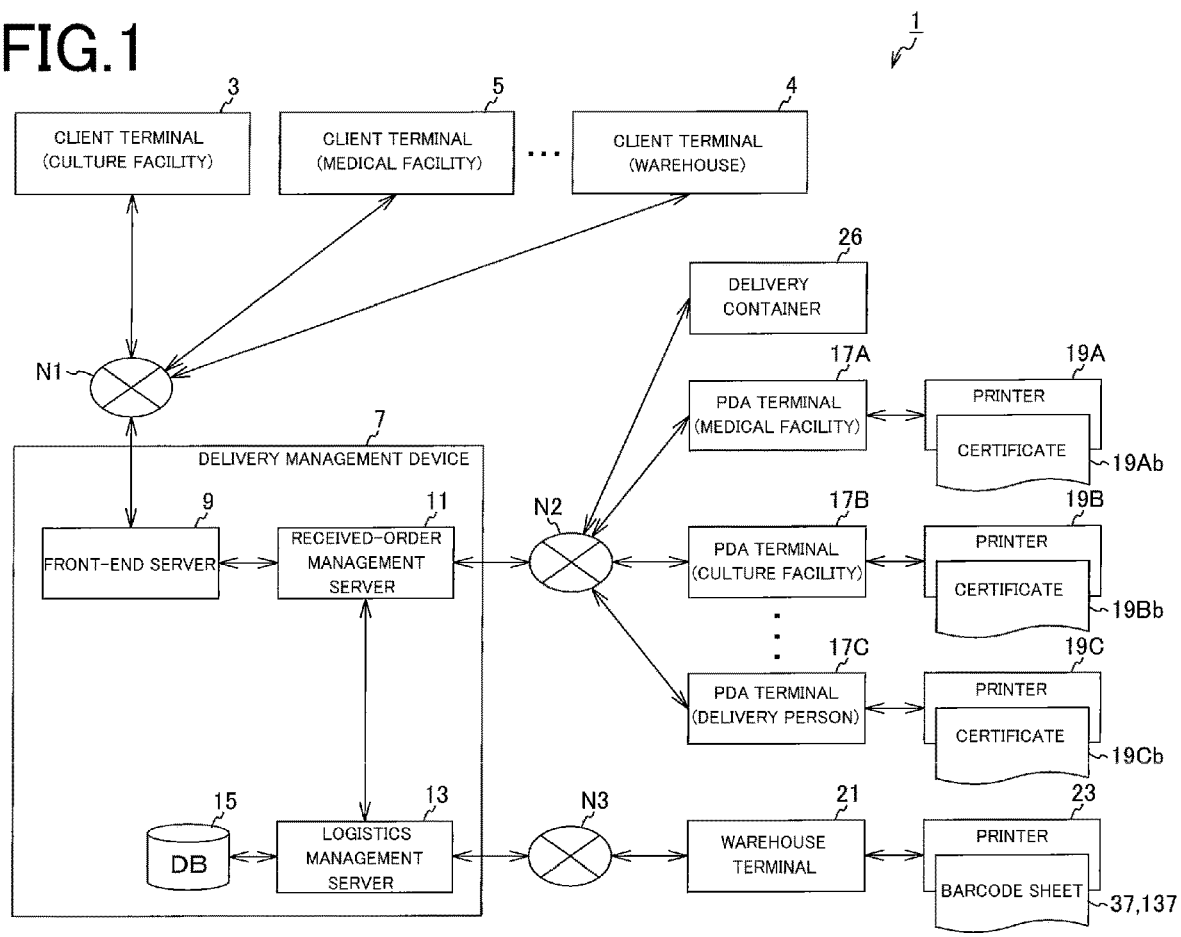
FIG. 1 is a block diagram illustrating a configuration of a delivery management system according to a first embodiment of the present invention.

The present invention is explained below in more detail by embodiments illustrated in the drawings.

The present invention has the following configuration for a regenerative medicine process in order to prevent mix-up of a plurality of different kinds of delivered articles without opening a delivery container and to automate a verification process.

That is, a delivery management system according to the present invention is characterized by including an article container that accommodates therein an article, a delivery container for accommodating therein the article container and delivering it, a delivery management device that generates barcode image data that specifies each of the article container and the delivery container, and a barcode sheet on which a barcode image is printed based on the barcode image data generated by the delivery management device. The barcode sheet includes a first barcode label indicating a serial number related to the article, a barcode-image portion indicating the serial number related to the article, and a second barcode label indicating a delivery-container ID related to the delivery container. When an article container to which the first barcode label separated from the barcode sheet is attached, the delivery container, and the barcode sheet from which the first barcode label has been separated reach a delivery destination, the article container is verified using the second barcode label attached to the delivery container and the barcode-image portion at the delivery destination.

By the above-described configuration, it is possible to prevent mix-up of a plurality of different kinds of delivered articles without opening a delivery container and to automate a verification process, for a regenerative medicine process.

Characteristics of the present invention described above are explained in detail with reference to the drawings mentioned below. Note that, unless otherwise specified, constituent elements, types, combinations, shapes, and relative arrangements thereof described in the following embodiments are not intended to limit the scope of the present invention solely thereto and are only explanatory examples.

Characteristics of the present invention described above are explained below in detail with reference to the drawings.

First Embodiment

<Delivery Management System>

FIG. 1 is a block diagram illustrating a configuration of a delivery management system according to a first embodiment of the present invention. In the following descriptions, explanations will be made while like constituent elements are denoted by like reference signs.

A delivery management system 1 includes a client terminal (culture facility) 3, a client terminal (warehouse) 4, a client terminal (medical facility) 5, communication networks N1, N2, and N3, a delivery management device 7, a delivery container 26, a PDA terminal 17A (medical facility), a PDA terminal 17B (culture facility), a PDA terminal 17C (delivery person), printers 19A, 19B, and 19C, a warehouse terminal 21, a printer 23, and a small terminal 27.

The delivery management device 7 includes a front-end server 9, a received-order management server 11, a logistics management server 13, and a database DB 15 and is operated by a delivery company.

In the present embodiment, each of the client terminals 3, 4, and 5, the delivery container 26, the PDA terminals 17A, 17B, and 17C, the printers 19A, 19B, and 19C, and the small terminal 27 is configured in plural. However, each of the elements may be configured in singular. Further, the communication network is divided into the communication networks N1, N2, and N3. However, these networks may be configured by the same network.

The front-end server 9 has a function of receiving data from the client terminals 3, 4, and 5 via the network N1 to provide a direct access service to the client terminals 3, 4, and 5 and change a display format.

The client terminal 3 is a terminal operable by a staff of a culture facility 35. The client terminal 4 is installed in a warehouse and is operable by a delivery person in the warehouse. The client terminal 5 is a terminal operable by a medical staff such as a doctor and a nurse in the medical facility.

The received-order management server 11 receives data of the small terminal 27 via the communication network N2 to manage the state of each delivery container 26.

The received-order management server 11 includes a ROM (Read Only Memory), a RAM (Random Access Memory), a CPU (Central Processing Unit), and an HDD (Hard Disk Drive), and reads an operating system OS from the HDD and then loads the OS on the RAM to activate the OS, and reads programs (programs illustrated in various flowcharts described later) from the HDD to perform various types of processing, under control of the OS.

The logistics management server 13 is arranged in each warehouse that stores therein each article or in each warehouse that stores therein a plurality of articles, and executes control for shipping a corresponding article to a medical facility or a culture facility that is a client upon reception of a request from the received-order management server 11.

The delivery container 26 receives GPS signals from respective GPS satellites, calculates location data based on the GPS signals, and transmits the location data with a device code unique to that delivery container 26 added thereto to the received-order management server 11 via the communication network N2.

The PDA terminals 17A, 17B, and 17C are portable information terminals each of which is connected to the received-order management server 11 and the logistics management server 13 via the network N2 to perform data communication, thereby transmitting image data and a print job to the printer 19, for example. The PDA terminals 17A, 17B, and 17C each read barcode information (ID) from a barcode image on a barcode sheet and transmit the barcode information to the received-order management server 11.

The printer 19 expands a print image in accordance with the image data and the print job received from the corresponding PDA terminal 17A, 17B, or 17C and prints image data including an image of a certificate on a recording medium 19Ab, 19Bb, or 19Cb.

The warehouse terminal 21 is a terminal operable by a staff in the warehouse and transmits image data and a print job received from the logistics management server 13 via the network N3 to the printer 23.

The printer 23 expands a print image in accordance with the image data and the print job received from the warehouse terminal 21 and prints image data including a barcode image on a barcode sheet 37 or 137.

The small terminal 27 is arranged on a side surface of the delivery container 26, acquires data such as the temperature and the humidity in the delivery container and the open/closed state of a lid 26a, which will be described later, and transmits the data to the received-order management server 11 via the network N2.

<Delivery Vehicle with Delivery Container Placed Thereon>

Figure 2:
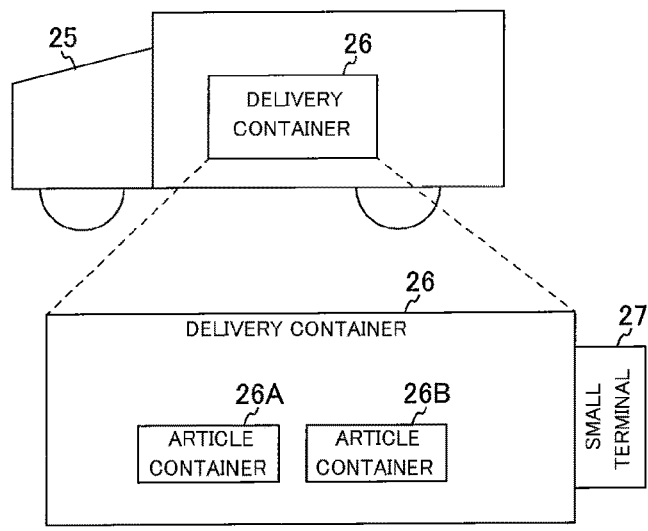
FIG. 2 is a perspective view illustrating a delivery vehicle on which a delivery container according to the first embodiment of the present invention is placed.

FIG. 2 is a perspective view illustrating a delivery vehicle on which the delivery container according to the first embodiment of the present invention is placed.

A delivery vehicle 25 includes the delivery container 26 placed on a loading platform thereof. Further, the delivery container 26 accommodates therein an article container 26A and an article container 26B. The small terminal 27 is provided on a side surface of the delivery container 26 to be in contact therewith.

A part of a tag string fastened to each of the article containers 26A and 26B accommodated in the delivery container 26 is pulled outside, and a tag is fastened at the end thereof.

The small terminal 27 is arranged to be in close contact with the side surface of the delivery container 26 and communicates with the received-order management server 11 via the network N2.

<Hardware Configuration of Delivery Container and Small Terminal>

Figure 3:
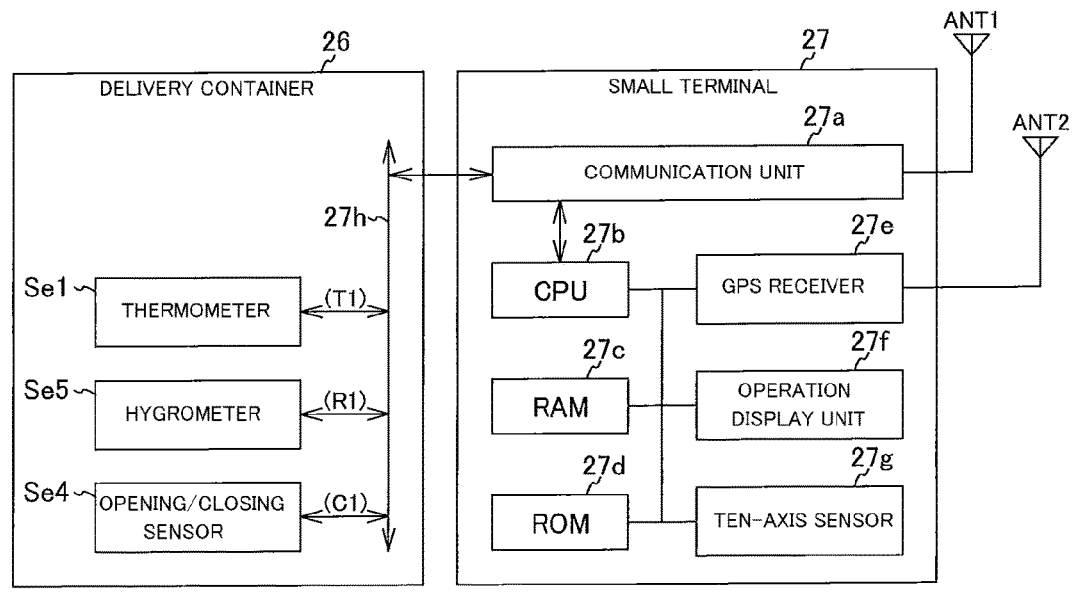
FIG. 3 is a diagram illustrating a hardware configuration of the delivery container and a small terminal according to the first embodiment of the present invention.

FIG. 3 is a diagram illustrating a hardware configuration of the delivery container and the small terminal according to the first embodiment of the present invention.

The delivery container 26 can accommodate a plurality of articles therein, includes various sensors Se1, Se4, and Se5 therein or attached to the outside thereof, and is connected to the small terminal 27 via a bus 27h.

The thermometer Se1 is provided in the delivery container 26, measures the ambient temperature in the delivery container 26, and outputs temperature data (T1) to a communication unit 27a.

An opening/closing sensor Se4 is provided in the delivery container 26, detects whether the lid 26a of the delivery container 26 is open or closed, and outputs opening/closing data (C1) to the communication unit 27a.

The hygrometer Se5 is provided in the delivery container 26, measures the ambient humidity in the delivery container 26, and outputs humidity data (R1) to the communication unit 27a.

The small terminal 27 includes the communication unit 27a, a CPU 27b, a RAM 27c, a ROM 27d, a GPS receiver 27e, an operation display unit 27f, and a ten-axis sensor 27g.

The communication unit 27a has an antenna ANT1 and transmits and receives data to and from the received-order management server 11 via the communication network N2.

The CPU 27b controls the entire operation of the small terminal 27, using the RAM 27c as a work memory, in accordance with a program memorized in advance in the ROM 27d.

The RAM 27c is a volatile memory medium capable of high-speed read and write of information and can be used as a work memory.

The ROM 27d is a read-only non-volatile memory medium and stores therein firmware and various kinds of data.

The GPS receiver 27e receives radio signals from a plurality of GPS satellites via an antenna ANT2 to calculate location information of a delivery container 26 and transmits the calculated location information to the received-order management server 11 via the communication network N2.

The operation display unit 27f includes a screen for displaying a menu for various types of setting and mode selection and key buttons, for example, and receives various types of operation requests from a user.

The ten-axis sensor 27g is an inertial measurement unit capable of performing ten-axis measurement and is a composite sensor in which a three-axis angular velocity sensor (a gyroscope), a three-axis accelerometer, a three-axis magnetic sensor, and a pressure sensor are sealed in one package. The ten-axis sensor 27g is arranged in the small terminal to be in contact with a side surface of the delivery container 26.

<PDA Terminal>

Figure 4:
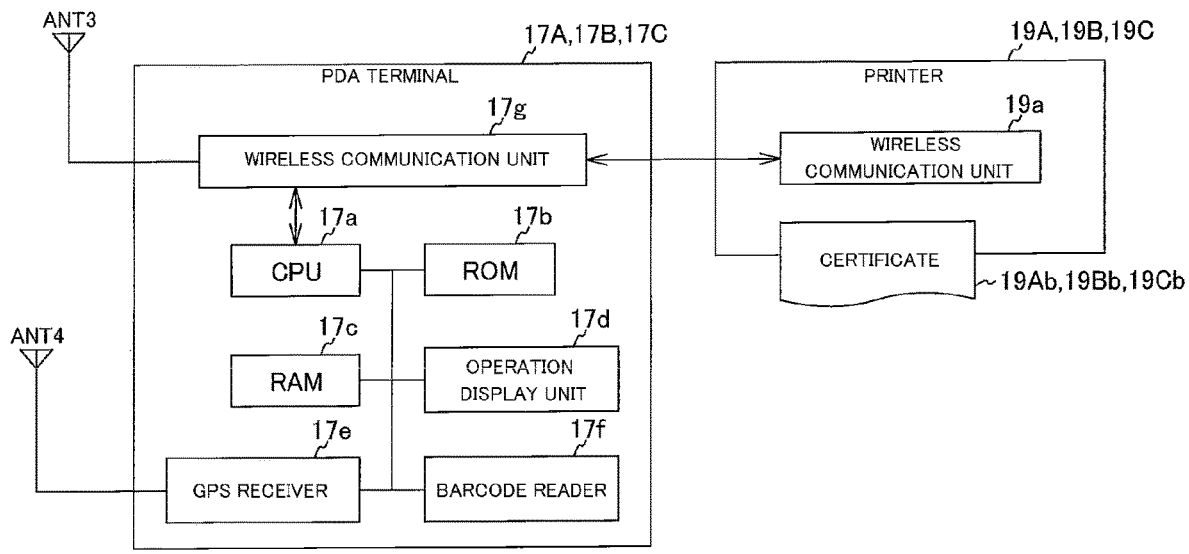
FIG. 4 is a diagram illustrating a hardware configuration of a PDA terminal (a portable information terminal) according to the first embodiment of the present invention.

FIG. 4 is a diagram illustrating a hardware configuration of the PDA terminal (the portable information terminal) according to the first embodiment of the present invention.

The PDA terminals 17A, 17B, and 17C each include a CPU 17a, a ROM 17b, a RAM 17c, an operation display unit 17d, a GPS receiver 17e, a barcode reader 17f, and a wireless communication unit 17g.

The CPU controls the entire operation of the PDA terminal using the RAM as a work memory, in accordance with a program memorized in advance in the ROM.

The ROM is a read-only non-volatile memory medium and stores therein firmware and various kinds of data.

The RAM is a volatile memory medium capable of high-speed read and write of information and can be used as a work memory.

The operation display unit 17d includes a screen for displaying a menu for various types of setting and mode selection and key buttons, for example, and receives various types of operation requests from a user. For example, a used state/unused state of each of the sensors (the various sensors Se1, Se4 and Se5) described later can be set from the operation display unit 27f.

The GPS receiver 17e receives radio signals from a plurality of GPS satellites via the antenna ANT2 to calculate location information of the PDA terminal and transmits the calculated location information to the received-order management server 11 via the communication unit.

The barcode reader 17f reads code information from a barcode image presented on a barcode sheet (a recording medium) or a display and outputs the code information to the CPU.

The wireless communication unit 17g transmits and receives data to and from a printer via, for example, WiFi communication.

The printers 19A, 19B, and 19C each include a wireless communication unit 19a, expands a print image in accordance with image data and a print job received from the PDA terminal 17A, 17B, or 17C, and prints image data on the recording medium 19Ab, 19Bb, or 19Cb.

<Warehouse Terminal>

Figure 5:
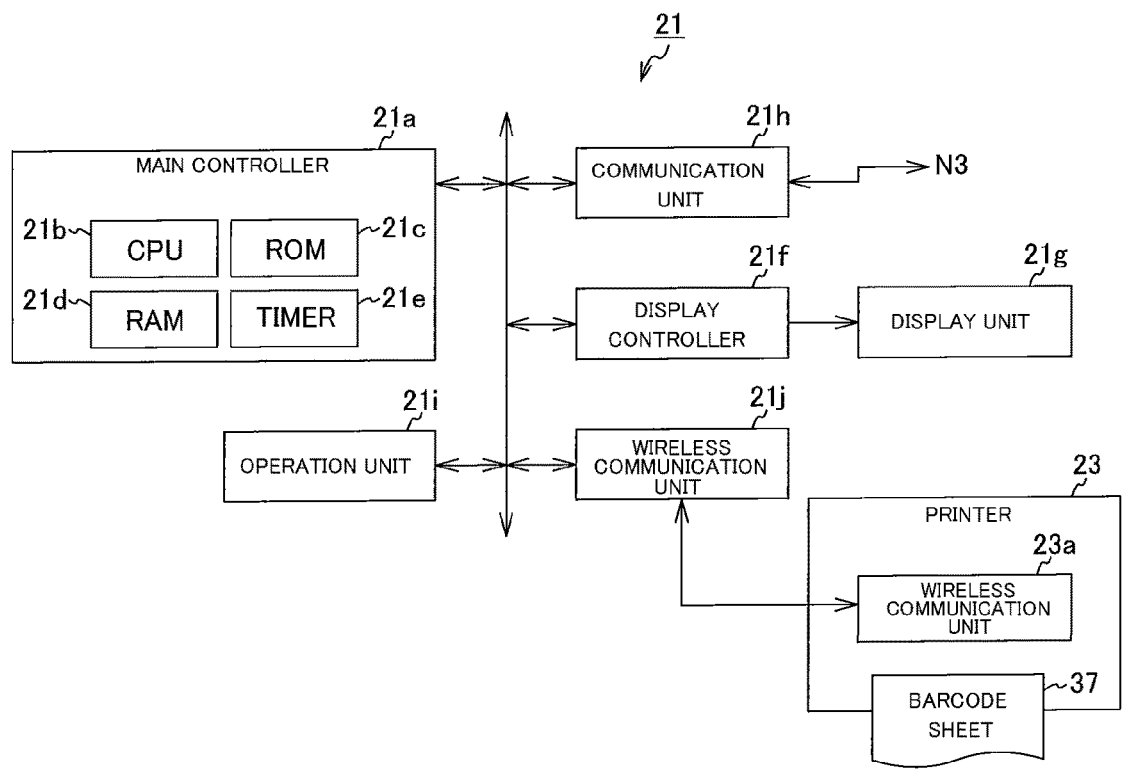
FIG. 5 is a diagram illustrating a hardware configuration of a warehouse terminal according to the first embodiment of the present invention.

FIG. 5 is a diagram illustrating a hardware configuration of the warehouse terminal according to the first embodiment of the present invention.

The warehouse terminal 21 is a personal computer and includes a main controller 21a, a display controller 21f, a display unit 21g, a communication unit 21h, an operation unit 21i, and a wireless communication unit 21j.

The main controller 21a includes a CPU (central processing unit) 21b, a ROM (read only memory) 21c, a RAM (random access memory) 21d, and a timer 21e therein. The CPU 21b reads an operating system OS from the ROM 21c and then loads the OS on the RAM 21d to activate the OS, and reads a program (a processing module) of application software from the ROM 21c to perform various types of processes, under control of the OS.

The display controller 21f draws an image input from the main controller 21a on a VRAM and causes the display unit 21g to display the image. The display unit 21g displays the image drawn on the VRAM by the display controller 21f.

The communication unit 21h is connected to another personal computer via the network N3.

The operation unit 21i includes a keyboard a mouse, and the like.

The wireless communication unit 21j transmits and receives data to and from the printer 23 via, for example, WiFi communication.

The printer 23 includes a wireless communication unit 23a, expands a print image in accordance with image data and a print job received from the warehouse terminal 21, and prints image data on the barcode sheet 37.

<Functional Blocks of Received-Order Management Server>

FIG. 6(a) is a functional block diagram of the delivery management system according to the first embodiment of the present invention. FIG. 6(b) is a functional block diagram of the PDA terminal according to the first embodiment of the present invention.

A regenerative medicine process K1 related to autologous cells includes a first delivery process K3 and a second delivery process K5.

In the first delivery process K3, a collected material collected from a human body in a medical facility 31 is accommodated in a container A (a container), and thereafter the container A (the container) is delivered to the culture facility 35.

In the second delivery process K5, a drug produced using the collected material in the culture facility 35 is accommodated in a container B (a second container) different from the container A (the container), and thereafter the container B (the second container) is delivered to the medical facility 31.

A controller 7s including a ROM, a RAM, and a CPU is provided in the delivery management device 7 illustrated in FIG. 1. The controller 7s reads an operating system OS from the ROM and then loads the OS on the RAM to activate the OS, and generates functional modules for reading programs from the ROM and performing various processes, under control of the OS. Each functional module is generated as a block in the controller 7s illustrated in FIG. 6.

The controller 7s of the delivery management device 7 illustrated in FIG. 6(a) includes a second communication unit 7a, a third communication unit 7b, a barcode-information generation unit 7c, a search unit 7d, and the database DB 15.

In each PDA terminal 17A, 17B, or 17C illustrated in FIG. 4, the ROM 17b, the RAM 17c, and the CPU 17a are provided. An operating system OS is read from the ROM 17b and then loaded on the RAM 17c to activate the OS, and generates functional modules for reading programs from the ROM 17b and performing various processes, under the control of the OS. The functional modules are generated as blocks illustrated in FIG. 6(b), respectively.

Each PDA terminal 17A, 17B, or 17C illustrated in FIG. 6(b) includes the barcode reader 17f, a verification unit 17s, and a first communication unit 17t.

The delivery management system 1 includes a drug wrapping (an article container) 140 that accommodates therein a drug as an article, the delivery container 26 for accommodating therein the drug wrapping (the article container) 140 and delivering it, the delivery management device 7 that generates barcode image data for specifying each of the drug wrapping (the article container) 140 and the delivery container 26, and the barcode sheet 137 on which a barcode image is printed based on the barcode image data generated by the delivery management device 7.

The barcode sheet 137 includes a barcode label 137c (a first barcode label) indicating a serial number (an article identification number) related to the drug as the article, a barcode-image portion 137e indicating the serial number related to the drug as the article, and barcode label 137d (a second barcode label) indicating a delivery-container ID related to the delivery container.

When the drug wrapping (the article container) 140 to which the barcode label 137c (the first barcode label) separated from the barcode sheet 137 is attached, the delivery container 26, and the barcode sheet 137 from which the barcode label 137c (the first barcode label) has been separated reach a delivery destination, the drug wrapping (the article container) 140 is verified using the second barcode label 137d attached to the delivery container and the barcode-image portion 137e at the delivery destination.

The delivery management system 1 includes the PDA terminal 17C (the portable information terminal) that is carried by a delivery person of a delivery company of the delivery container and communicates with the delivery management device 7 via a communication network.

The PDA terminal 17C (the portable information terminal) includes the barcode reader 17f that reads barcode information from the barcode-image portion 137e, the first communication unit 17t that receives a first serial number related to an article from the delivery management device 7, and the verification unit 17s that verifies whether the first serial number received from the delivery management device 7 and a second serial number related to an article read from the barcode-image portion 137e on the barcode sheet 137 match each other.

As for the barcode sheet 37, an article container to which the first barcode label 37c separated from the barcode sheet 37 is attached, the delivery container 26 to which the second barcode label 37b separated from the barcode sheet 37 is attached, and the barcode sheet 37 from which those barcode labels have been separated are delivered to the delivery destination.

The delivery management system 1 may include the PDA terminal 17C (the portable information terminal) that is carried by a delivery person of a delivery company of the delivery container and communicates with the delivery management device 7 via a communication network.

The PDA terminal 17C (the portable information terminal) may include the barcode reader 17f that reads barcode information from a barcode image, the first communication unit 17t that transmits a delivery-container ID read from the barcode label 37d attached to the delivery container 26 to the delivery management device 7 and receives the first serial number related to an article corresponding to that delivery-container ID from the delivery management device 7, and the verification unit 17s that verifies whether the first serial number received from the delivery management device 7 and the second serial number related to an article read from the barcode-image portion 37e on the barcode sheet 37 match each other.

The delivery management system 1 includes the PDA terminal 17C (the portable information terminal) that is carried by a delivery person of a delivery company of the delivery container and communicates with the delivery management device 7 via a communication network.

The PDA terminal 17C (the portable information terminal) includes the barcode reader 17f that reads barcode information from a barcode image, the first communication unit 17t that transmits a delivery-container ID read from the barcode label 37d attached to the delivery container 26 to the delivery management device 7 and receives the first serial number related to an article corresponding to that delivery-container ID from the delivery management device 7, and the verification unit 17s that verifies whether the first serial number received from the delivery management device 7 and the second serial number related to an article container read from the barcode-image portion 37e on the barcode sheet 37 match each other.

The delivery management system 1 includes the PDA terminal 17 that is carried by a medical staff who collects an article or a person involved in manufacturing in a culture facility processing the article and that communicates with the delivery management device 7 via a communication network.

The PDA terminal 17 includes the barcode reader 17f that reads barcode information from a barcode image, the first communication unit 17t that transmits a delivery-container ID read from a barcode label attached to the delivery container to the delivery management device 7 and receives the first article identification number corresponding to that delivery-container ID from the delivery management device 7, and the verification unit 17s that verifies whether the first article identification number received from the delivery management device 7 and the second article identification number related to an article container read from the article container match each other.

In the delivery management system 1, the first barcode label 37c and the barcode-image portion 37e provided on the barcode sheet may each have one identical barcode image indicating an article identification number related to a collected material and be printed on the barcode sheet 37 for the number of collected materials.

The barcode label 137c (the first barcode label) and the barcode-image portion 137e provided on the barcode sheet 137 each have one identical barcode image indicating a serial number related to a drug and are printed on the barcode sheet 137 for the number of drugs.

The barcode label 37c (the first barcode label) is attached to a collection container 39A or 39B accommodating therein a collected material.

The barcode label 137c (the first barcode label) is attached to the drug wrapping 140 accommodating therein a drug.

The barcode sheet 37 includes the second barcode label indicating a delivery-container ID related to the delivery container 26 and the third barcode label 37c indicating a collection-container ID related to the collection container 39.

When the delivery container 26 to which the second barcode label separated from the barcode sheet 37 is attached, the article container to which the third barcode label 37c separated from the barcode sheet 37 is attached, and the barcode sheet 37 from which those barcode labels have been separated reach a delivery destination, verification is performed using the second barcode label 37d attached to the delivery container 26 and the third barcode label 37c attached to the article container at the delivery destination.

The barcode label 137c may be attached to a tag that can be attached to a drug package 139A, as a fourth barcode label.

The delivery management system 1 may include the PDA terminal 17C (the portable information terminal) that is carried by a delivery person of a delivery company of the delivery container and communicates with the delivery management device 7 via a communication network.

The PDA terminal 17C (the portable information terminal) may include the first communication unit 17t that transmits a delivery-container ID read from the barcode label 37d attached to the delivery container 26 to the delivery management device 7 and receives the first article identification number corresponding to that delivery-container ID from the delivery management device 7, and the verification unit 17s that verifies whether the first article identification number received from the delivery management device 7 and a second article identification number related to an article container read from the article container match each other.

The third barcode label 37c is printed for the number of collected materials on the barcode sheet 37.

The third barcode label 37c is attached to the collection container 39.

The delivery management device 7 includes the barcode-information generation unit 7c that generates a barcode image indicating an article identification number related to an article container, a barcode image indicating a delivery-container ID related to the delivery container 26, and a barcode image indicating a serial number related to an article.

The delivery management device 7 includes the database DB15 that memorizes a serial number related to an article to be accommodated in an article container and a delivery-container ID related to the delivery container 26 in association with each other, the second communication unit 7a that receives a delivery-container ID read from the barcode label 37d attached to the delivery container 26 from the portable information terminal, and the search unit 7d that searches a serial number in the database 15 by using the received delivery-container ID as a key.

The second communication unit 7a transmits the serial number acquired from the database DB15 to the PDA terminal 17C (the portable information terminal).

The delivery management device 7 includes the database DB15 that memorizes an article identification number related to an article container and a delivery-container ID related to the delivery container 26 in association with each other, the second communication unit 7a that receives a delivery-container ID read from the barcode label 37d attached to the delivery container 26 from the PDA terminal 17C (the portable information terminal), and the search unit 7d that searches an article identification number in the database DB15 by using the received delivery-container ID as a key.

The second communication unit 7a transmits the article identification number acquired from the database DB15 to the PDA terminal 17C (the portable information terminal).

The delivery management system 1 includes the warehouse terminal 21 that receives a shipping instruction from the third communication unit 7b of the delivery management device 7 and transmits a request for generating a barcode image to the third communication unit 7b of the delivery management device 7 in response to the shipping instruction.

The warehouse terminal 21 prints a barcode image received from the barcode-information generation unit 7c of the delivery management device 7 on the barcode sheet 37.

The verification unit 17s transmits the verification result to the delivery management device 7.

The delivery management system 1 includes the delivery vehicle 25 that delivers the delivery container 26.

The delivery vehicle 25 performs delivery for the regenerative medicine process K1 related to autologous cells including the first delivery process K3 and the second delivery process K5, delivers the delivery container 26 with a collected material placed thereon from a medical facility to a culture facility as the first delivery process K3, and delivers the delivery container 26 with a drug placed thereon from the culture facility to the medical facility as the second delivery process K5.

<Sequence Diagram from Patient Registration to Advance Delivery to Medical Facility>

Figure 7:
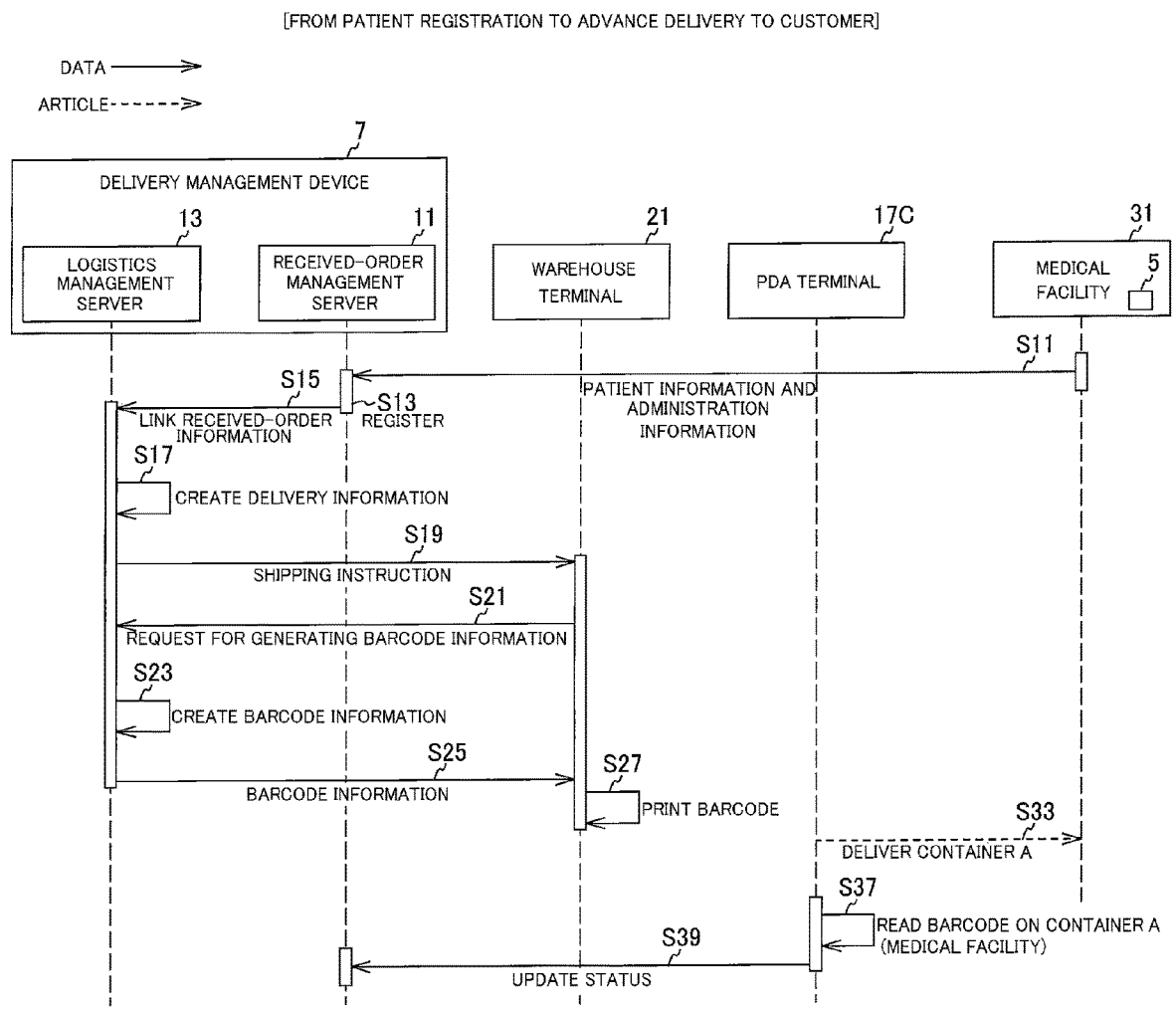
FIG. 7 is a sequence diagram from patient registration to advance delivery to a medical facility according to the first embodiment of the present invention.

FIG. 7 is a sequence diagram from patient registration to advance delivery to a medical facility according to the first embodiment of the present invention. Solid arrows illustrated in FIG. 7 indicate flow of data and broken arrows indicate flow of materials.

In the medical facility 31 illustrated in FIG. 7, there is the body of a patient who needs treatment, and a nurse, for example, collects a specimen such as bone marrow or blood from the body of the patient.

At Step S11, the client terminal 5 in the medical facility 31 requests image data of a personal calendar to the received-order management server 11. The received-order management server 11 transmits screen data of a generated personal calendar to the client terminal 5 in the medical facility 31. The client terminal 5 displays the personal calendar, inputs patient information and administration information to the personal calendar, and transmits the patient information and the administration information to the received-order management server 11 to register the information.

At Step S13, the received-order management server 11 receives the patient information and the administration information from the client terminal 5 and registers the patient information and the administration information in a database.

At Step S15, the received-order management server 11 transmits the patient information and the administration information received from the client terminal 5 to the logistics management server 13 and requests the logistics management server 13 to link received-order information.

At Step S17, the logistics management server 13 creates delivery information based on the received-order information.

At Step S19, the logistics management server 13 transmits a shipping instruction to the warehouse terminal 21.

At Step S21, the warehouse terminal 21 that has received the shipping instruction transmits a request for barcode information to the logistics management server 13.

At Step S23, the logistics management server 13 creates the barcode information.

At Step S25, the logistics management server 13 transmits the created barcode information to the warehouse terminal 21.

At Step S27, the warehouse terminal 21 that has received the barcode information prints a barcode image on a sheet to create a barcode sheet.

At Step S33, a delivery person who holds the PDA terminal 17C delivers the container A to the medical facility 31.

At Step S37, the PDA terminal 17C carried by the delivery person in the medical facility reads barcode information from the barcode image on the barcode sheet attached to the container A by using the barcode reader 17f to acquire a delivery-container ID, a collection management ID, and a status (advance delivery).

At Step S39, the PDA terminal 17C transmits the delivery-container ID and the collection management ID to the received-order management server 11, in addition to status information indicating advance delivery. The received-order management server 11 that has received the status information, the delivery-container ID, and the collection management ID updates a collected-material-delivery-container status file F5 and a collection-container status file F7.

<Procedure of Delivering Container A from Medical Facility to Culture Facility>

Figure 8:
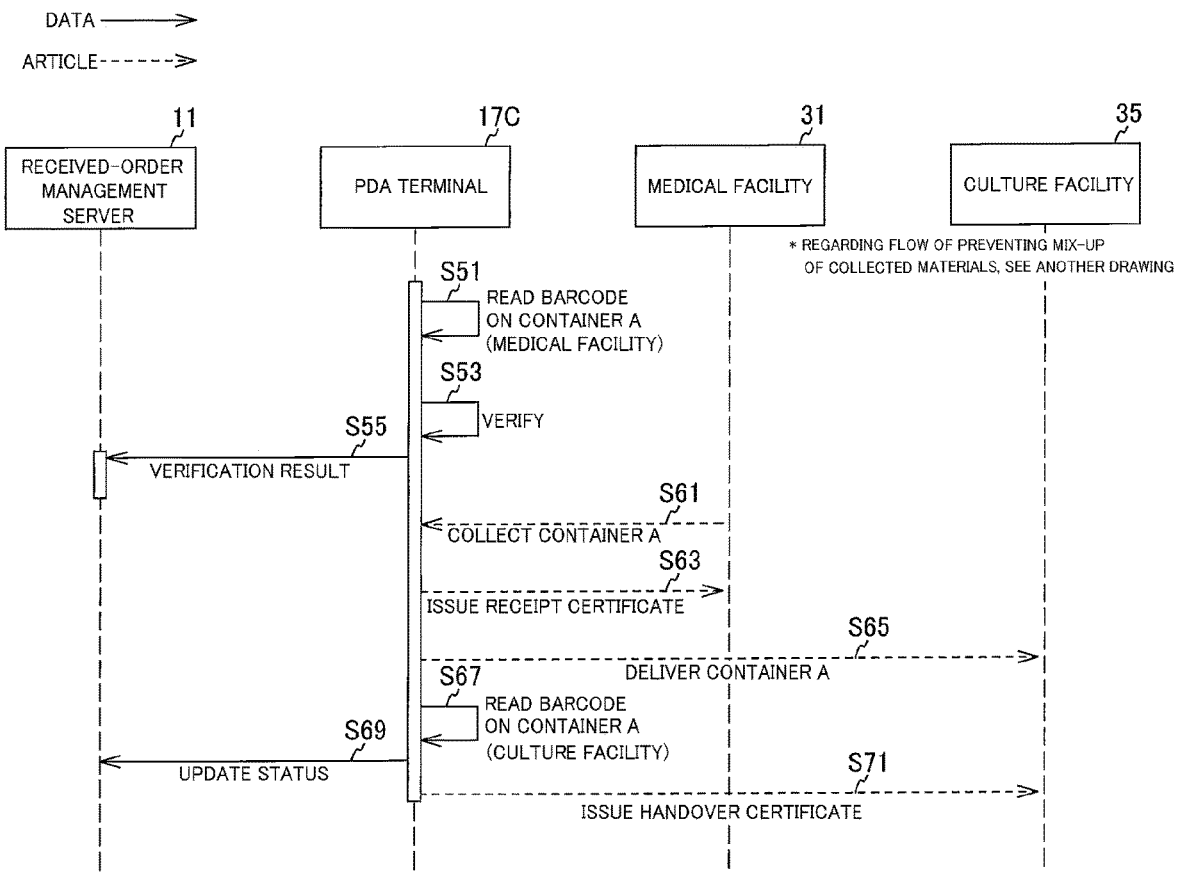
FIG. 8 is a sequence diagram illustrating a procedure of delivering a container A from a hospital facility to a culture facility.

FIG. 8 is a sequence diagram illustrating a procedure of delivering the container A from a medical facility to a culture facility. Solid arrows illustrated in FIG. 8 indicate flow of data and broken arrows indicate flow of materials.

At Step S51, the PDA terminal 17C carried by a delivery person in the medical facility 31 reads barcode information from a barcode image on a barcode sheet attached to the container A by using the barcode reader 17f to acquire a delivery-container ID, a collection management ID, and a status (collection).

At Step S53, the PDA terminal 17 performs verification (FIG. 14) by using the barcode information (the delivery-container ID and the collection management ID) read from the container A as a key.

At Step S55, the result (match/mismatch) of the verification performed by the PDA terminal 17 is transmitted to the received-order management server 11.

At Step S61, the container A is collected in the medical facility 31 by a delivery person.

At Step S63, the PDA terminal 17 issues a receipt certificate indicating that the container A has been collected. The receipt certificate is passed to a staff of the medical facility 31 by a delivery person.

At Step S65, the delivery person delivers the collected container A to the culture facility 35.

At Step S67, the PDA terminal 17 carried by the delivery person in the culture facility 35 reads the barcode information from the barcode image on the barcode sheet attached to the container A by using the barcode reader 17f to acquire the delivery-container ID and the collection management ID.

At Step S69, the PDA terminal 17 transmits the barcode information (the delivery-container ID and the collection management ID) to the received-order management server 11. The received-order management server 11 that has received the barcode information updates the collected-material-delivery-container status file F5 and the collection-container status file F7.

At Step S71, the PDA terminal 17 issues a handover certificate indicating that the container A has been delivered to the medical facility 31 by a delivery person. The handover certificate is passed to a staff of the medical facility 31 by a delivery person.

The handover certificate describes a human-body ID and the delivery-container ID that can be visually confirmed.

<ER Diagram>

Figure 9:
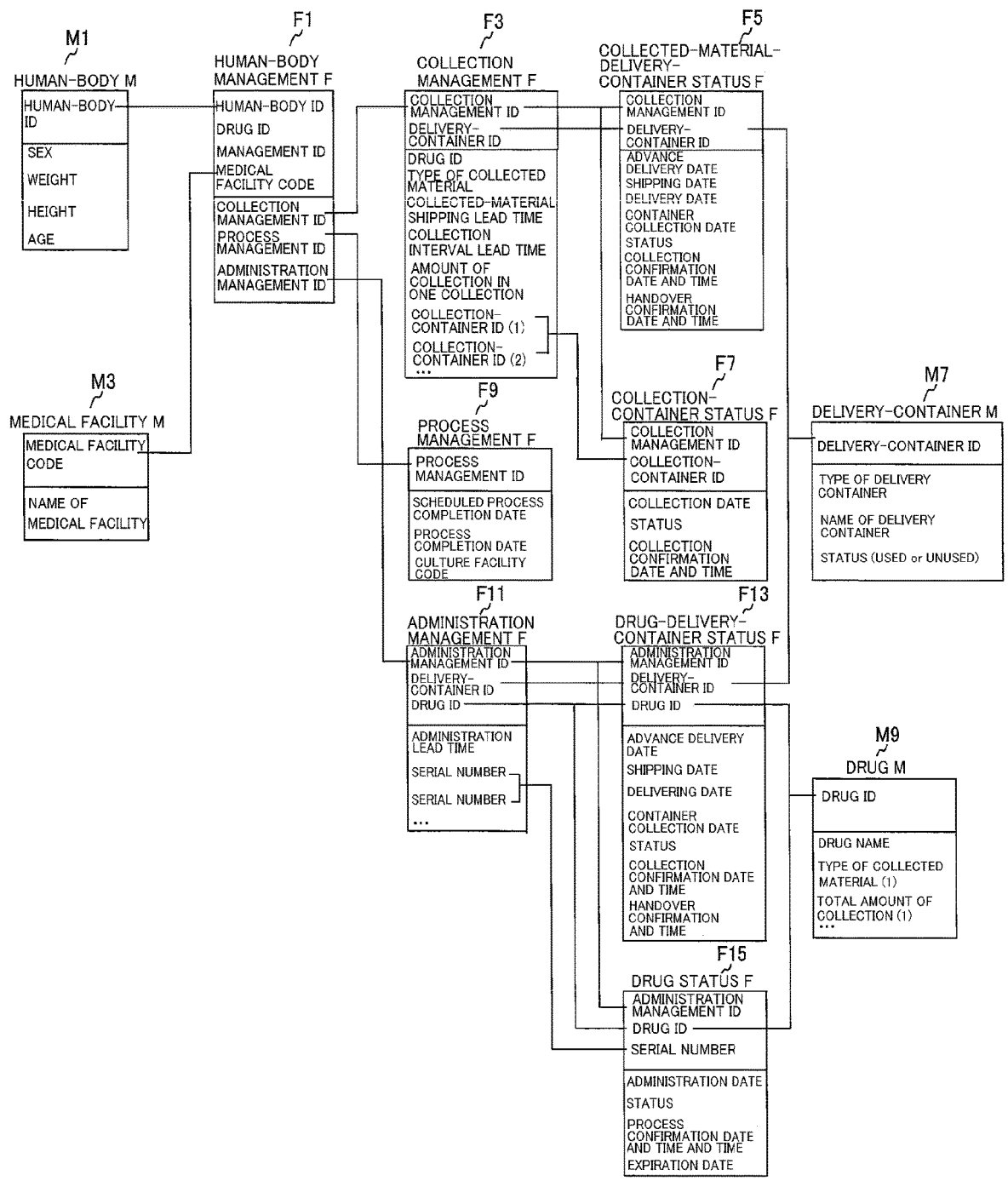
FIG. 9 is an ER diagram illustrating configurations and association of files and masters to be managed by a received-order management server according to the first embodiment of the present invention.

FIG. 9 is an ER diagram illustrating configurations and association of files and masters to be managed by the received-order management server according to the first embodiment of the present invention. In FIG. 9, the sign F denotes a file, and the sign M denotes a master.

<Human-Body Master>

The received-order management server 11 memorizes the sex, the weight, the height, and the age of a human body in a human-body master M1 in association with a human-body ID.

The received-order management server 11 extracts the sex, the weight, the height, and the age of the human body from the human-body master M1 by using the human-body ID as a key.

<Medical Facility Master>

The received-order management server 11 memorizes the name of a medical facility in a medical facility master M3 in association with a medical facility code.

The received-order management server 11 extracts the name of a medical facility from the medical facility master M3 by using the medical facility code as a key.

<Human-Body Management File>

The received-order management server 11 memorizes a collection management ID, a process management ID, and an administration management ID in a human-body management file F1 in association with a human-body ID, a drug ID, a management ID, and a medical facility code.

The received-order management server 11 extracts the collection management ID, the process management ID, and the administration management ID from the human-body management file F1 by using the human-body ID, the drug ID, the management ID, and the medical facility code as a key.

<Collection Management File>

The received-order management server 11 memorizes a drug ID, the type of collected material, a collected-material shipping lead time, a collection interval lead time, the amount in one collection, and at least one collection-container ID in a collection management file F3 in association with a collection management ID and a delivery-container ID.

The received-order management server 11 extracts the drug ID, the type of collected material, the collected-material shipping lead time, the collection interval lead time, the amount in one collection, and at least one of the collection-container IDs from the collection management file F3 by using the collection management ID and the delivery-container ID as a key.

<Collected-Material-Delivery-Container Status File>

In the collected-material-delivery-container status file F5, an advance delivery date, a shipping date, a delivery date, a container collection date, the status, a collection confirmation date and time, and a handover confirmation date and time of a delivery container are memorized in association with a collection management ID and a delivery-container ID.

The received-order management server 11 extracts the advance delivery date, the shipping date, the delivery date, the container collection date, the status, the collection confirmation date and time, and the handover confirmation date and time of the delivery container from the collected-material-delivery-container status file F5 by using the collection management ID and the delivery-container ID as a key.

<Collection-Container Status File>

A collection date, the status, and a collection confirmation date and time of a collected material are extracted in a collection-container status file F7 in association with a collection management ID and a collection-container ID.

The received-order management server 11 extracts the collection date, the status, and the collection confirmation date and time of the collected material from the collection-container status file F7 by using the collection management ID and the collection-container ID as a key.

<Process Management File>

In a process management file F9, a scheduled process completion date, a process completion date, and a culture facility code are memorized in association with a process management ID.

The received-order management server 11 extracts the scheduled process completion date, the process completion date, and the culture facility code from the process management file F9 by using the process management ID as a key.

<Administration Management File>

In an administration management file F11, an administration lead time and a serial number are memorized in association with an administration management ID, a delivery-container ID, and a drug ID.

The received-order management server 11 extracts the administration lead time and the serial number from the administration management file F11 by using the administration management ID, the delivery-container ID, and the drug ID as a key.

<Drug-Delivery-Container Status File>

In a drug-delivery-container status file F13, an advance delivery date, a shipping date, a delivering date, a container collection date, the status, a collection confirmation date and time, and a handover confirmation date and time of a delivery container for delivering a drug are memorized in association with an administration management ID, a delivery-container ID, and a drug ID.

The received-order management server 11 extracts the advance delivery date, the shipping date, the delivering date, the container collection date, the status, the collection confirmation date and time, and the handover confirmation date and time of the delivery container for delivering the drug from the drug-delivery-container status file F13 by using the administration management ID, the delivery-container ID, and the drug ID as a key.

<Drug Status File>

In a drug status file F15, an administration date, the status, a process confirmation date and time, and an expiration date of a drug are memorized in association with an administration management ID, a drug ID, and a serial number.

The received-order management server 11 extracts the administration date, the status, the process confirmation date and time, and the expiration date of the drug from the drug status file F15 by using the administration management ID, the drug ID, and the serial number as a key.

<Delivery-Container Master>

In a delivery-container master M7, the type of delivery container, the name of the delivery container, and the status indicating used or unused are memorized in association with a delivery-container ID.

The received-order management server 11 extracts the type of delivery container, the name of the delivery container, and the status indicating used or unused from the delivery-container master M7 by using the delivery-container ID as a key.

<Drug Master>

In a drug master M9, a drug name, the type of collected material, and the total collected amount are memorized in association with a drug ID.

The received-order management server 11 extracts a drug name, the type of collected material, and the total collected amount from the drug master M9 by using the drug ID as a key.

<Association Between Files>

Here, association between files is described with reference to the ER diagram illustrated in FIG. 9.

(1) Association Between Human-Body Management File F1 and Each Management File F In the human-body management file F1, a medical facility, a human body, and a drug to be administered are associated with each other and are memorized with a management ID assigned thereto.

In the human-body management file F1, the entire process is divided into three processes including a collection process of collecting cells, a processing process of processing the collected cells, and an administration process of administering a processed drug, which are managed with management IDs respectively assigned thereto in order to administer a target drug to the body of a patient.

A collection management ID is used for identifying information related to collection, a process management ID is assigned to information related to processing, and an administration management ID is assigned to information related to administration. Those pieces of information are managed by using the management IDs in the human-body management file F1.

(2) Association Between Collection Management File F3, Collected-Material-Delivery-Container Status File F5, and Collection-Container Status File F7

In the collection management file F3, a delivery-container ID for delivering a collected material is memorized in association with the collection management ID.

A collection-container ID used for identifying a collection container in which a collected material is stored is associated with the collection management ID and the delivery-container ID and is memorized.

In the collected-material-delivery-container status file F5, an advance delivery date, a shipping date, a delivery date, a container collection date, the status, a collection confirmation date and time, and a handover confirmation date and time of a delivery container are memorized in association with the collection management file F3 by using the collection management ID and the delivery-container ID.

In the collection-container status file F7, a collection date, the status, and a collection confirmation date and time of a collected material are memorized in association with the collection management file F3 by using the collection management ID and the collection-container ID.

(3) Association of Administration Management File F11, Drug-Delivery-Container Status File F13, and Drug Status File F15

In the administration management file F11, a delivery-container ID used for identifying a delivery container for delivering a drug is memorized in association with an administration management ID.

A serial number of a drug is memorized in association with the administration management ID, the delivery-container ID, and a drug ID.

In the drug-delivery-container status file F13, an advance delivery date, a shipping date, a delivering date, a container collection date, the status, a collection confirmation date and time, and a handover confirmation date and time of the delivery container are memorized in association with the administration management file F11 by using the administration management ID, the delivery-container ID, and the drug ID.

In the drug status file F15, an administration date, the status, a process confirmation date and time, and an expiration date of a drug are memorized by using the administration management ID, the drug ID, and the serial number.

<Process of Generating Barcode-Sheet Print Information>

Figure 10:
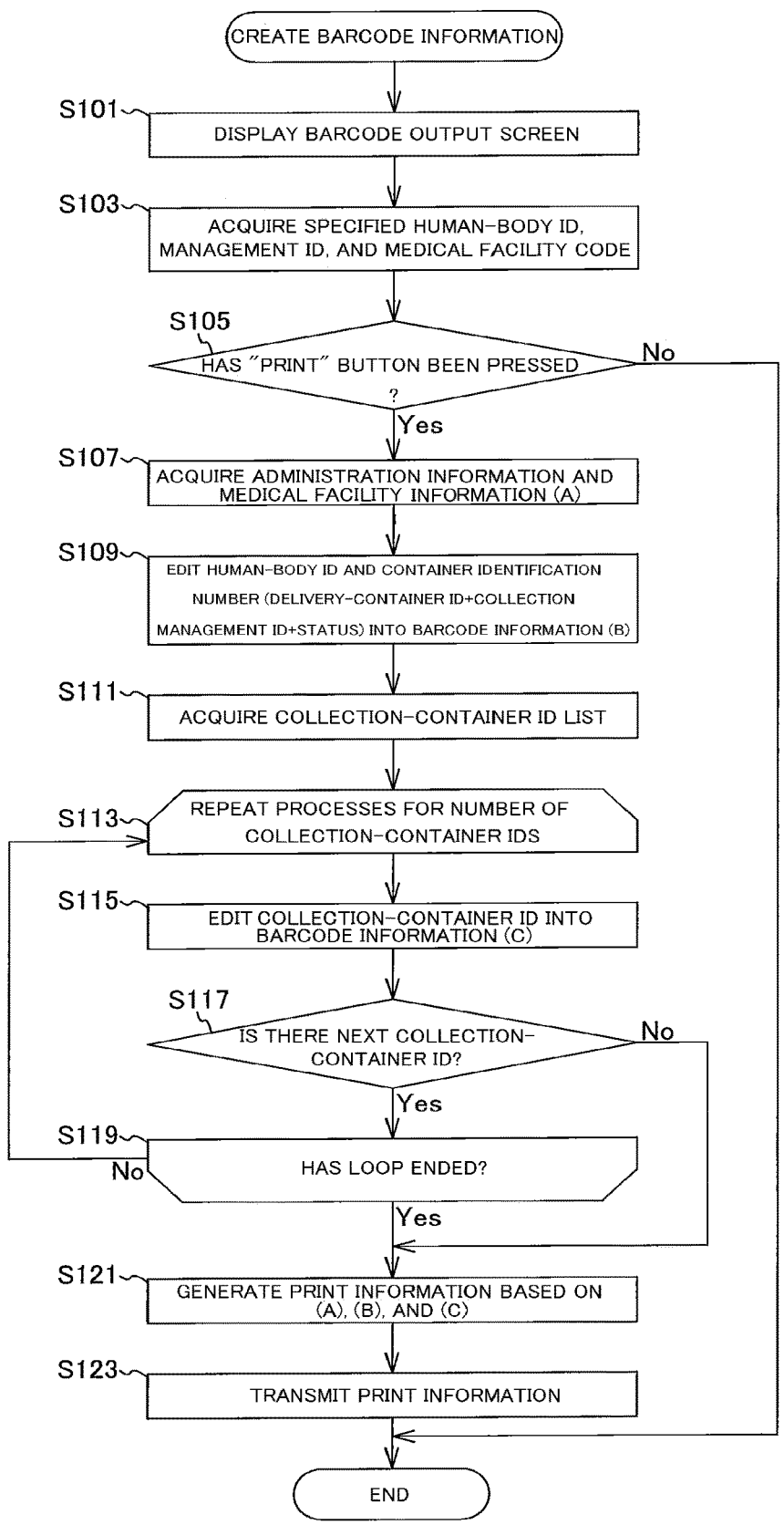
FIG. 10 is a flowchart illustrating a process of generating a barcode print information by a logistics management server according to the first embodiment of the present invention.

FIG. 10 is a flowchart illustrating a process of generating barcode print information by the logistics management server according to the first embodiment of the present invention, and illustrates a detailed process at Step S23 illustrated in FIG. 7.

At Step S101, the logistics management server 13 transmits a barcode output screen (not illustrated) to the warehouse terminal 21 and causes the warehouse terminal 21 to display the barcode output screen.

At Step S103, the logistics management server 13 acquires a human-body ID, a management ID, and a medical facility code specified from the warehouse terminal 21 via the barcode output screen.

At Step S105, the logistics management server 13 determines whether a "PRINT" button has been pressed by an operation by a delivery person via the barcode output screen (not illustrated). When the "PRINT" button has been pressed, the process proceeds to Step S107. When the "PRINT" button has not been pressed, the process is ended.

At Step S107, the logistics management server 13 acquires administration information and medical facility information (A).

At Step S109, the logistics management server 13 edits the acquired human-body ID and a container identification number (delivery-container ID+collection management ID+status) into barcode information (B).

At Step S111, the logistics management server 13 acquires a list of collection-container IDs from the collection management file F3 by using the delivery-container ID specified via the barcode output screen and the acquired collection management ID as a key.

At Step S113, the logistics management server 13 repeats the processes for the number of collection-container IDs.

At Step S115, the logistics management server 13 edits the acquired collection-container ID into barcode information (C).

At Step S117, the logistics management server 13 determines whether there is the next collection-container ID. When there is the next collection-container ID, the process proceeds to Step S119. When there is no next collection-container ID, the process proceeds to Step S121.

At Step S119, the logistics management server 13 determines whether a loop has ended. When the logistics management server 13 determines that the loop has not ended, the process returns to Step S113. When the logistics management server 13 determines that the loop has ended, the process proceeds to Step S121.

At Step S121, the logistics management server 13 generates barcode print information based on the edited data ((A), (B), and (C)).

At Step S123, the logistics management server 13 transmits the generated barcode print information to the warehouse terminal 21.

<Barcode Sheet>

FIG. 11 is a diagram illustrating overview of the barcode sheet according to the first embodiment of the present invention.

Barcode images are printed on the barcode sheet 37 as illustrated in FIG. 11, by the barcode sheet print process illustrated in FIG. 10.

As illustrated in FIG. 11, the barcode labels 37a, 37b, 37c, and 37d are arranged on the barcode sheet 37 printed in accordance with a collection management ID. Each of those labels can be separated from the barcode sheet 37.

(1) A barcode image corresponding to a human-body ID is printed on the barcode label 37a. The collection management ID is printed below the barcode label 37a.

(2) The barcode label 37b is a label to be attached to the delivery container 26 and includes a barcode image corresponding to a delivery-container ID printed thereon. The barcode label 37b is used in advance transportation of a container.

(3) The barcode label 37c is a label to be attached to each collection container 39 and includes the barcode-image portion 37e corresponding to each collection-container ID printed thereon. The barcode label 37c is printed for the number of the collection containers.

(4) The barcode-image portion 37e is a barcode-image portion in which a barcode image corresponding to a collection-container ID is printed, and is printed on the sheet 37 for the number of the barcode labels 37c. Each barcode-image portion 37e cannot be separated from the barcode sheet 37.

(5) The barcode label 37d is a label to be attached to the delivery container 26 together with the barcode label 37b and includes a barcode image corresponding to a delivery-container ID printed thereon.

<List of Data Output Source of Barcode Sheet>

FIG. 12 is a diagram illustrating a list of data output source of the barcode sheet according to the first embodiment of the present invention. The meaning of each item mentioned on the barcode sheet 37 is described.

A medical facility ID indicates a medical facility code managed by the medical facility M3.

The name of a medical facility indicates the name of a medical facility managed by the medical facility M3.

A scheduled collection date indicates a collection date managed by the collection-container status file F7.

A human-body ID indicates a human-body ID managed by the human-body management file F1.

A human-body ID barcode indicates a human-body ID managed by the human-body management file F1.

A collection management ID indicates a collection management ID managed by the collection management file F3.

A delivery-container ID for advance transportation of delivery container indicates a delivery-container ID managed by the collection management file F3.

A container identification barcode for advance transportation of delivery container indicates a delivery-container ID managed by the collection management file F3, a collection management ID managed by the collection management file F3, and a status managed by the collected-material-delivery-container status file F5.

A barcode for collection of collection container indicates a collection-container ID (n) managed by the collection management file F3.

A delivery-container ID for collection of delivery container indicates a delivery-container ID managed by the collection management file F3.

A container identification barcode for collection of delivery container indicates a delivery-container ID managed by the collection management file F3, a collection management ID managed by the collection management file F3, and a status in the collected-material-delivery-container status file F5.

<Barcode Label and Target to which Barcode Label is Attached>

Figure 13:
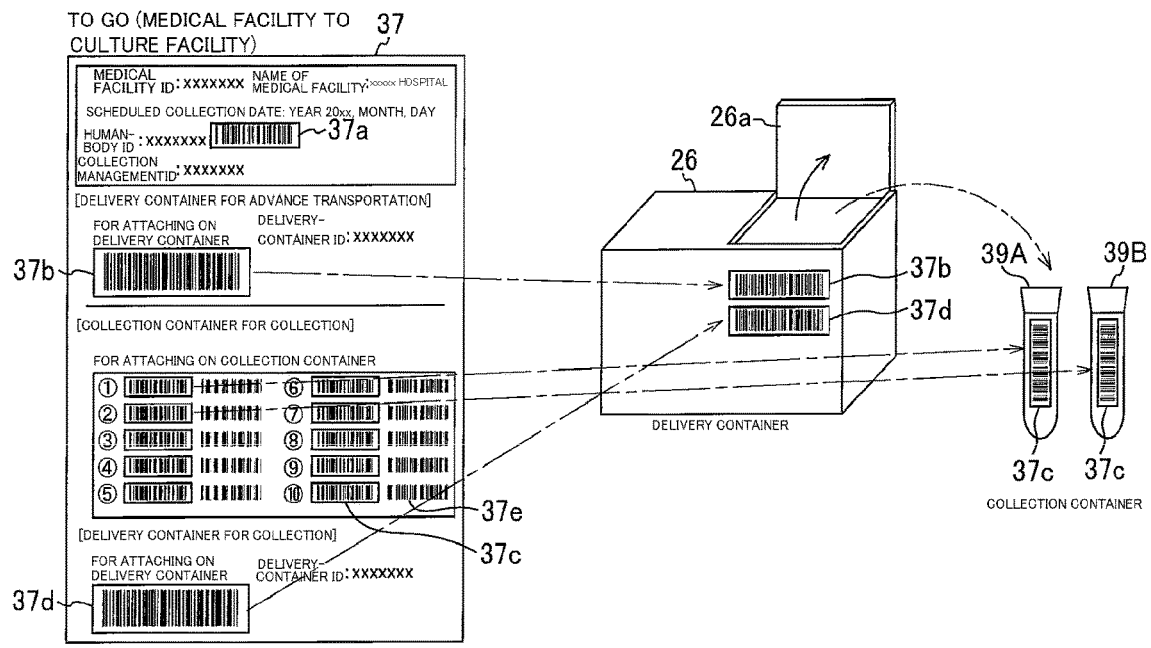
FIG. 13 is a schematic diagram illustrating a barcode label according to the first embodiment of the present invention and a container to which the barcode label is attached.

FIG. 13 is a schematic diagram illustrating the barcode label according to the first embodiment of the present invention and a container to which the barcode label is attached.

The barcode labels 37b and 37d separated from the barcode sheet 37 by a delivery person are attached to a side surface of the delivery container 26. Further, the barcode labels 37c and 37c separated from the barcode sheet 37 by the delivery person are attached to side surfaces of the collection containers 39A and 39B, respectively.

<Procedure for Preventing Mix-Up of Collected Materials>

Figure 14:
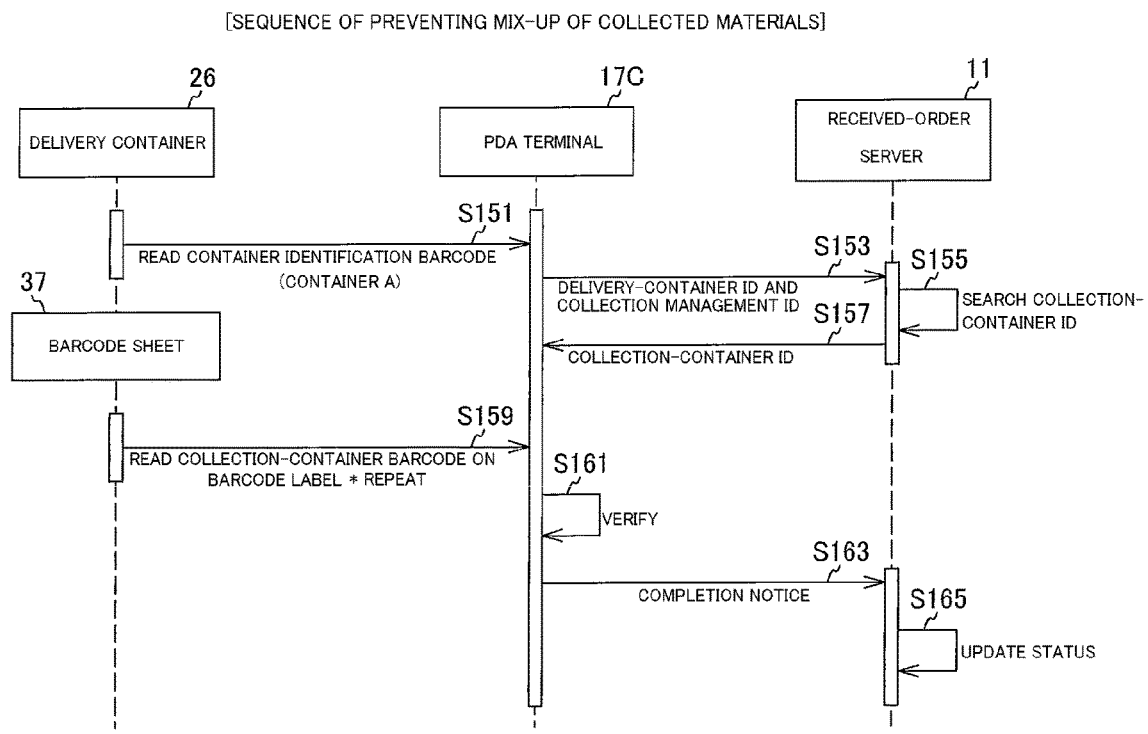
FIG. 14 is a sequence diagram illustrating a procedure from process completion to advance delivery to a culture facility which is managed by a delivery management system according to a second embodiment of the present invention.

FIG. 14 is a sequence diagram illustrating a mix-up prevention procedure for preventing a medical staff or a delivery person from accommodating a collected material in a container other than a specified container, which is managed by the delivery management system according to the first embodiment of the present invention.

At Step S151, a delivery person reads, from a barcode image on the barcode label 37d attached to the delivery container 26, its barcode information by using the barcode reader 17f provided in the PDA terminal 17C to acquire its container identification barcode information.

At Step S153, the PDA terminal 17C transmits a delivery-container ID and a collection management ID read from the delivery container 26 to the received-order management server 11.

At Step S155, the received-order management server 11 performs search in the collection management file F3 by using the delivery-container ID and the collection management ID received from the PDA terminal 17C as a key to acquire a collection-container ID corresponding thereto.

At Step S157, the received-order management server 11 transmits the acquired collection-container ID to the PDA terminal 17C.

At Step S159, the delivery person reads, from a barcode image in the barcode-image portion 37e printed on the barcode sheet 37, collection-container barcode information by using the barcode reader 17f provided in the PDA terminal 17C to acquire its collection-container ID.

At Step S161, the PDA terminal 17C verifies whether the collection-container ID acquired from the received-order management server 11 and the collection-container ID acquired from the barcode-image portion 37e match each other and confirms whether the IDs match each other to obtain a verification result (match/mismatch).

At Step S163, the PDA terminal 17C adds a completion notice to the verification result (match/mismatch) and transmits them to the received-order management server 11.

At Step S165, the received-order management server 11 updates the status in each of the collected-material-delivery-container status file F5 and the collection-container status file F7 (FIG. 9) based on the verification result (match/mismatch) received from the PDA terminal 17C.

Second Embodiment

<Procedure from Registration of Process Completion to Advance Delivery to Culture Facility>

Figure 15:
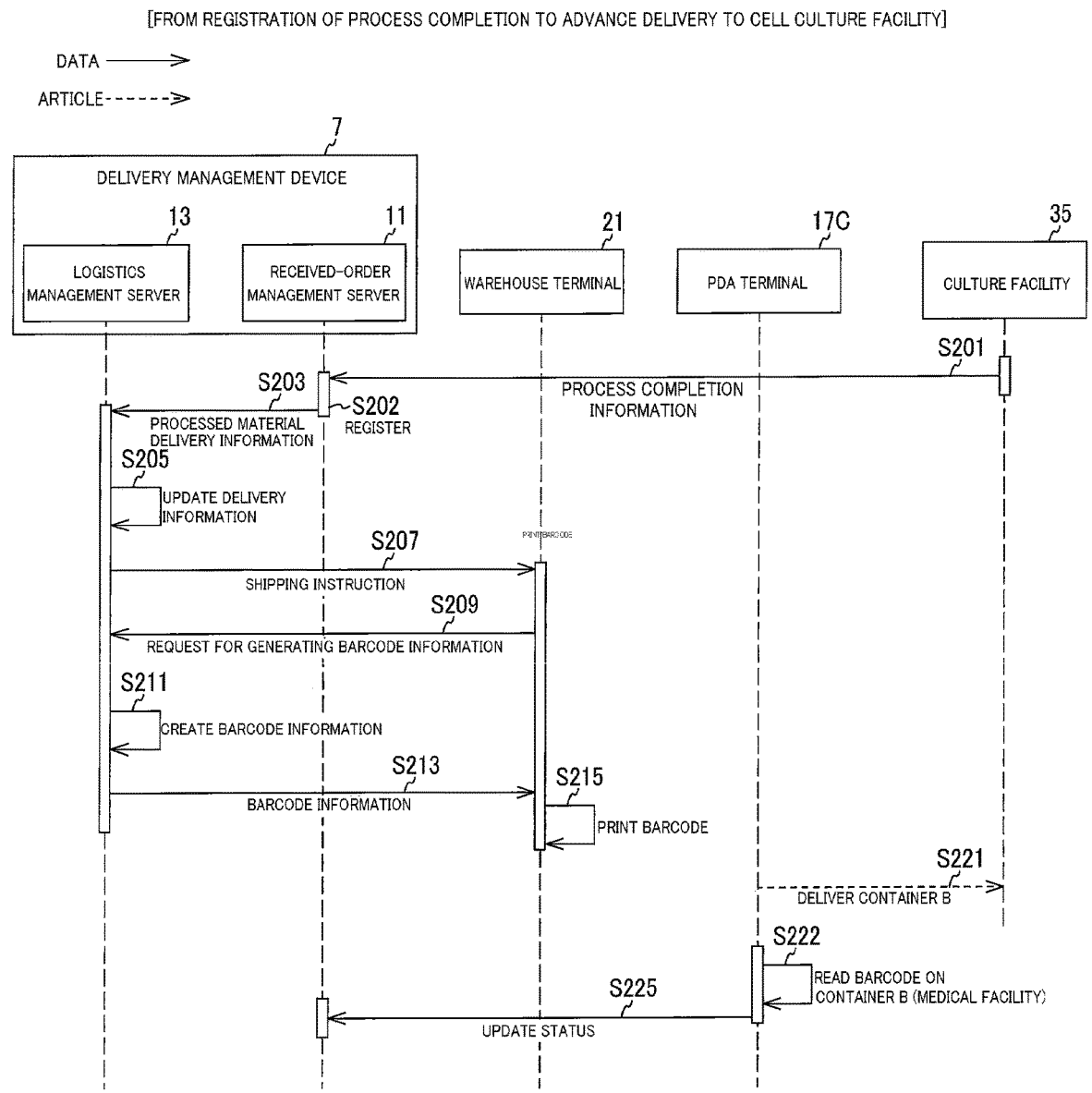
FIG. 15 is a sequence diagram illustrating a procedure from collection from a cell culture facility to delivery to a medical facility according to the second embodiment of the present invention.

FIG. 15 is a sequence diagram illustrating a procedure from process completion to advance delivery to a culture facility, which is managed by a delivery management system according to a second embodiment of the present invention.

At Step S201, processing completion information is transmitted to the received-order management server 11 by using the client terminal 3 in the culture facility 35.

At Step S202, the received-order management server 11 receives the processing completion information from the client terminal 3 and registers the process completion information in a database.

At Step S203, the received-order management server 11 transmits processed-material delivering information to the logistics management server 13.

At Step S205, the logistics management server 13 updates delivery information.

At Step S207, the logistics management server 13 transmits a shipping instruction to the warehouse terminal 21.

At Step S209, the warehouse terminal 21 requests barcode information to the warehouse terminal 21 in order to prepare shipping of the container B in response to the shipping instruction received from the logistics management server 13.

At Step S211, the logistics management server 13 creates the barcode information in response to the request for the barcode information.

At Step S213, the logistics management server 13 transmits the barcode information to the warehouse terminal 21.

At Step S215, the warehouse terminal 21 prints a barcode image indicating the barcode information received from the logistics management server 13 on a sheet.

At Step S221, a delivery person who carries the PDA terminal 17C delivers the container B to the culture facility 35.

At Step S222, in a medical facility, the delivery person reads the barcode information from a barcode image on the barcode label 137b attached to the delivery container 26 by using the barcode reader 17f provided in the PDA terminal 17C to acquire a delivery-container ID, an administration management ID, and a drug ID corresponding thereto.

At Step S225, the PDA terminal 17C transmits status information to the received-order management server 11. The received-order management server 11 that has received the status information updates the drug-delivery-container status file F13 and the drug status file F15.

<Procedure from Collection from Cell Culture Facility to Delivery to Medical Facility>

Figure 16:
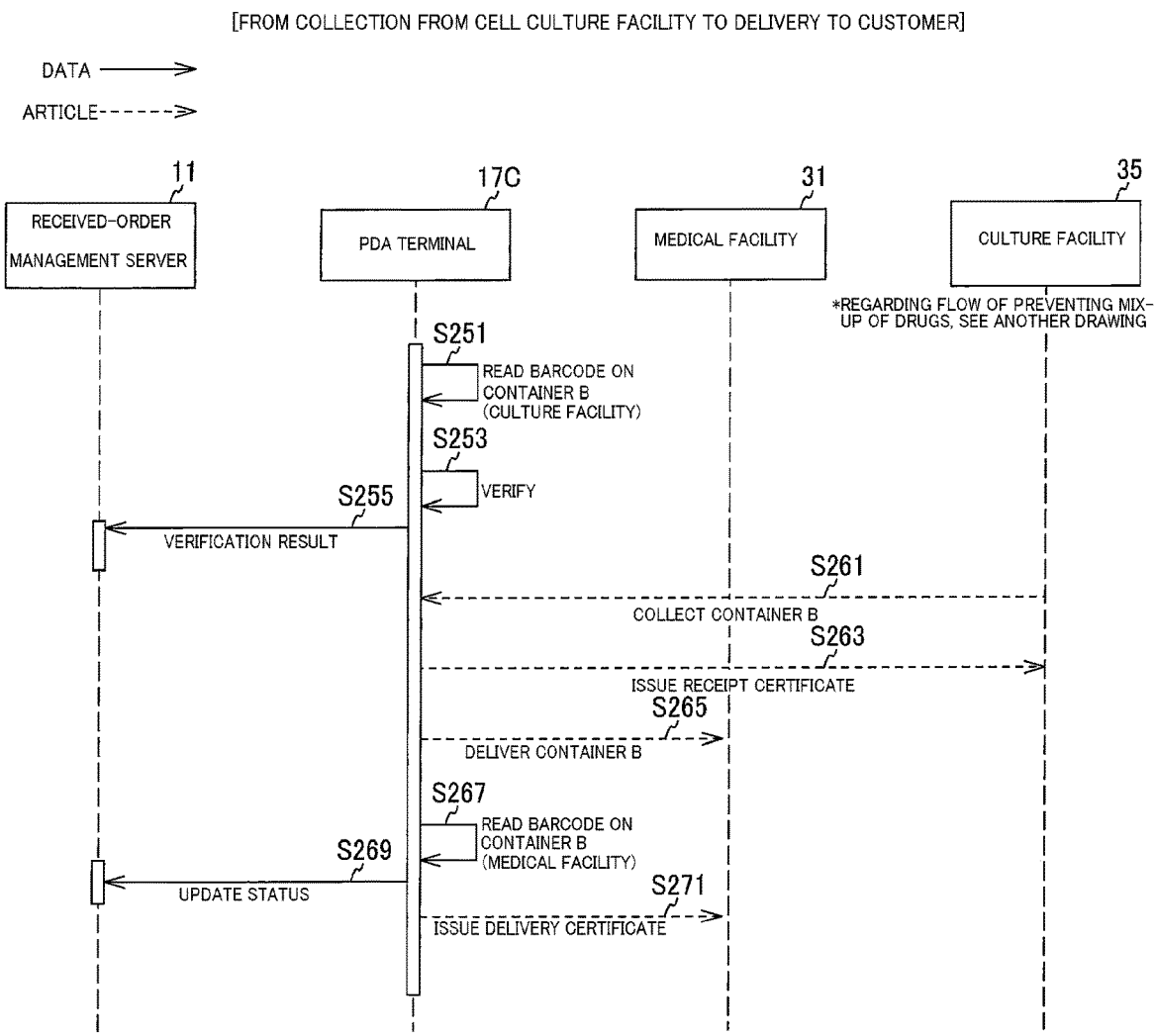
FIG. 16 is a sequence diagram illustrating a procedure from collection from the cell culture facility to delivery to the medical facility according to the second embodiment of the present invention.

FIG. 16 is a sequence diagram illustrating a procedure from collection from a cell culture facility to delivery to a medical facility according to the second embodiment of the present invention. Solid arrows illustrated in FIG. 16 indicate flow of data, and broken arrows indicate flow of articles.

At Step S251, the PDA terminal 17 carried by a delivery person in the culture facility 35 reads, from a barcode image on a barcode label attached to the container B, barcode information by using the barcode reader 17f to acquire a delivery-container ID, an administration management ID, a drug ID, and a status.

At Step S253, the PDA terminal 17 performs verification (FIG. 21) using the barcode information (the delivery-container ID and the collection management ID) read from the container B as a key.

At Step S255, the PDA terminal 17C transmits the result (match/mismatch) of the verification performed by the PDA terminal 17 to the received-order management server 11.

At Step S261, the container B is collected in the culture facility 35.

At Step S263, the PDA terminal 17 issues a receipt certificate indicating that the container B has been collected. The receipt certificate is passed to a staff of the culture facility 35.

At Step S265, the PDA terminal 17 delivers the collected container B to the medical facility 31.

At Step S267, the PDA terminal 17 carried by the delivery person in the medical facility 31 reads the barcode information from the barcode image on the barcode label 137 attached to the container B by using the barcode reader 17f to acquire the delivery-container ID, an administration management ID, the drug ID, and the status.

At Step S269, the PDA terminal 17 transmits the barcode information (the delivery-container ID, the administration management ID, the drug ID, and the status) to the received-order management server 11. The received-order management server 11 that has received the barcode information updates the drug-delivery-container status file F13 and the drug status file F15.

At Step S271, the PDA terminal 17 issues a delivery certificate indicating that the container B has been delivered to the medical facility 31. The delivery certificate is passed to a staff of the medical facility 31.

<Process of Printing Barcode Sheet>

Figure 17:
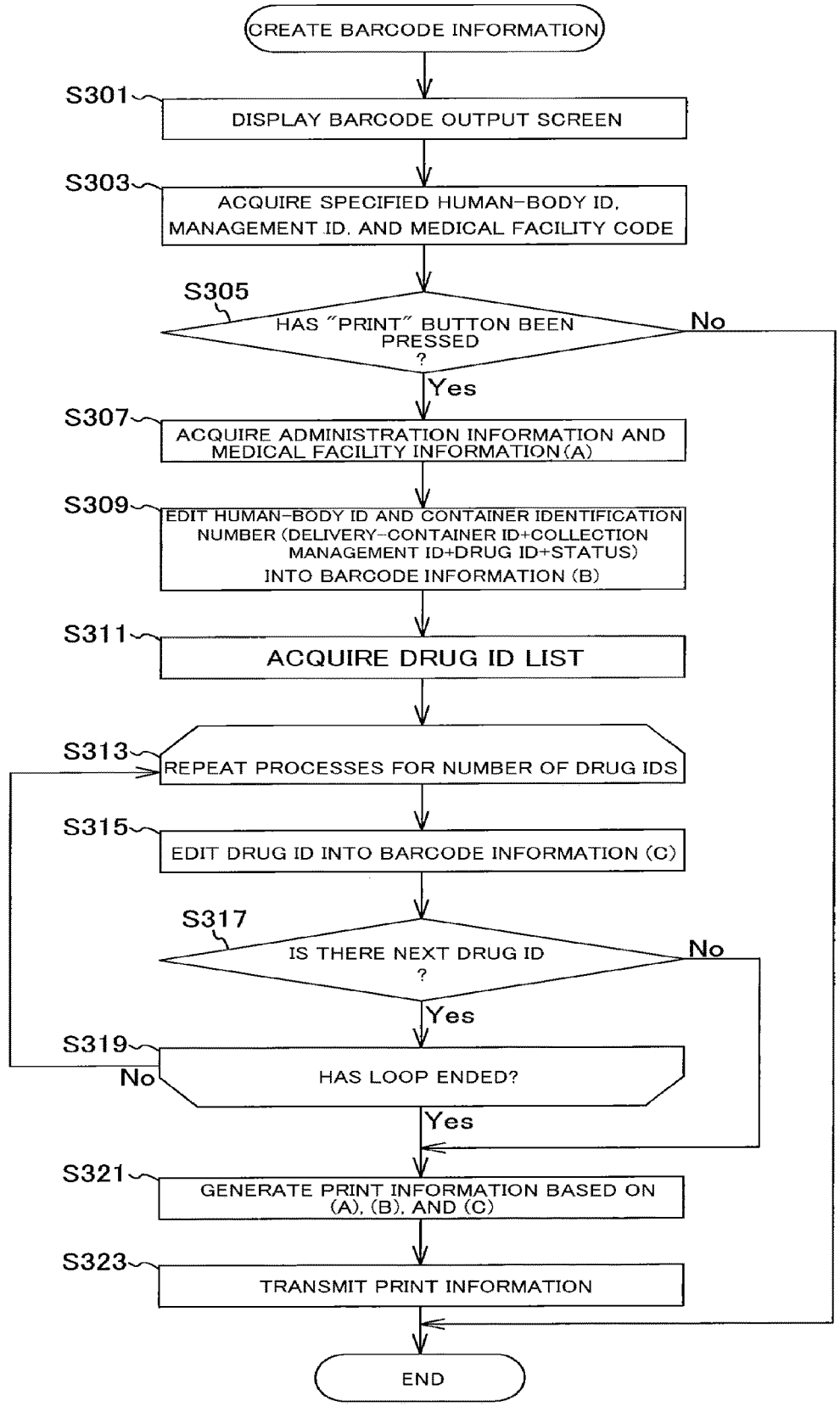
FIG. 17 is a flowchart illustrating a process of generating barcode print information by a logistics management server according to the second embodiment of the present invention.

FIG. 17 is a flowchart illustrating a process of generating barcode print information by the logistics management server according to the second embodiment of the present invention and illustrates a detailed process at Step S211 in FIG. 15.

At Step S301, the logistics management server 13 transmits a barcode output screen (not illustrated) to the warehouse terminal 21 and causes the warehouse terminal 21 to display the barcode output screen.

At Step S303, the logistics management server 13 acquires a human-body ID, a management ID, and a medical facility code specified from the warehouse terminal 21 via the barcode output screen.

At Step S305, the logistics management server 13 determines whether a "PRINT" button has been pressed by an operation by a delivery person via the barcode output screen (not illustrated). When the "PRINT" button has been pressed, the process proceeds to Step S307. When the "PRINT" button has not been pressed, the process is ended.

At Step S307, the logistics management server 13 acquires administration information and medical facility information (A).

At Step S309, the logistics management server 13 edits the acquired human-body ID and a container identification number (delivery-container ID+collection management ID+drug ID+status) into barcode information (B).

At Step S311, the logistics management server 13 acquires a list of drug IDs from the administration management file F11 by using the delivery-container ID and the drug ID specified via the barcode output screen and the acquired administration management ID as a key.

At Step S313, the logistics management server 13 repeats the processes for the number of drug IDs.

At Step S315, the logistics management server 13 edits the acquired drug ID into the barcode information (C).

At Step S317, the logistics management server 13 determines whether there is the next drug ID. When there is the next drug ID, the process proceeds to Step S319. When there is no next drug ID, the process proceeds to Step S321.

At Step S319, the logistics management server 13 determines whether a loop has ended. When the logistics management server 13 determines that the loop has not ended, the process returns to Step S313. When the logistics management server 13 determines that the loop has ended, the process proceeds to Step S321.

At Step S321, the logistics management server 13 generates the barcode print information based on the edited data ((A), (B), and (C)).

At Step S323, the logistics management server 13 transmits the generated barcode print information to the warehouse terminal 21.

<Barcode Sheet>

Figure 18:
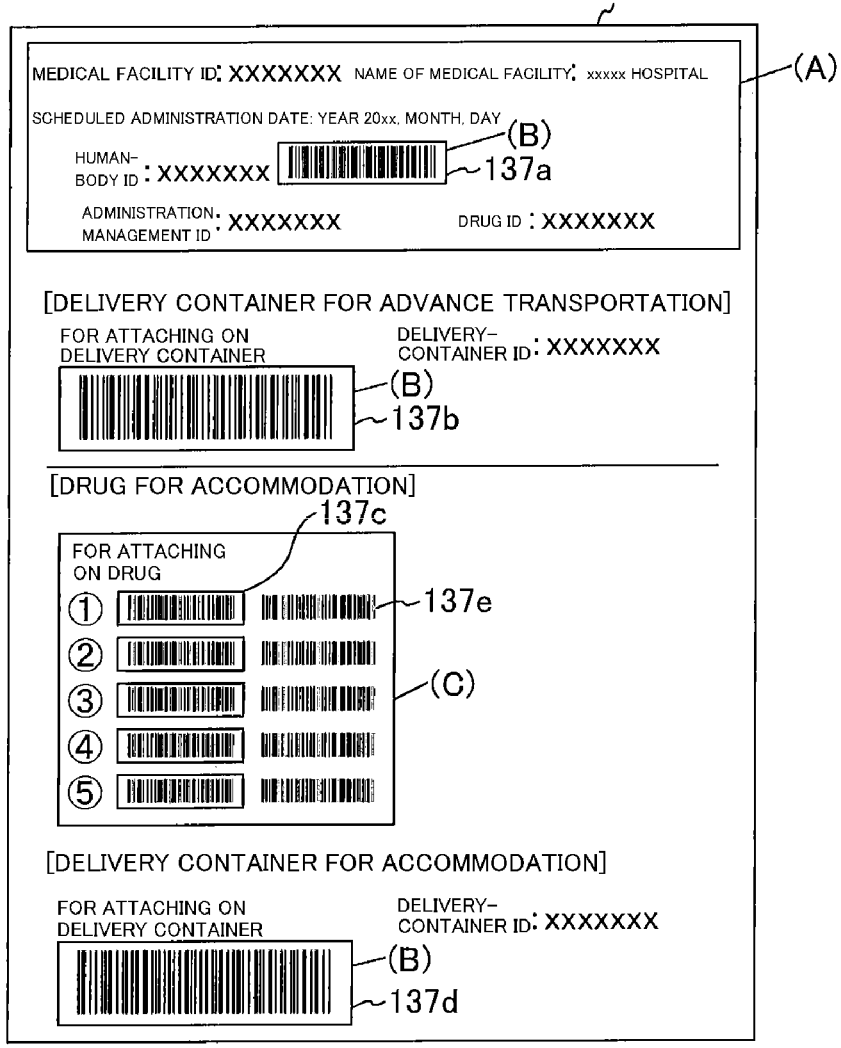
FIG. 18 is a diagram illustrating overview of a barcode sheet according to the second embodiment of the present invention.

FIG. 18 is a diagram illustrating overview of the barcode sheet according to the second embodiment of the present invention.

Barcode images are printed on a sheet illustrated in FIG. 18 by the barcode-sheet print process illustrated in FIG. 17.

As illustrated in FIG. 18, the barcode labels 137a, 137b, 137c, and 137d are arranged on the barcode sheet 137 printed in accordance with a collection management ID. Each label can be separated from the barcode sheet 137.

(1) A barcode image corresponding to a human-body ID is printed on the barcode label 137*a*. An administration management ID and a drug ID are printed below the barcode label 137*a*.

(2) The barcode label 137*b* is a label to be attached to a delivery container and includes a barcode image corresponding to a delivery-container ID printed thereon. The barcode label 137*b* is used in advance transportation of a container.

(3) The barcode label 137*c* is a detachable label to be attached to a drug wrapping (a plastic bag) and includes a barcode image printed thereon. The barcode image corresponds to a serial number of a drug assigned to each drug. The barcode label 137*c* is printed for the number of drugs.

(4) A barcode image corresponding to the serial number of the drug is printed in the barcode-image portion 137*e*. The number of the barcode-image portions 137*e* printed on the barcode sheet 137 is the same as the number of the barcode labels 137*c*. Each barcode-image portion 137*e* cannot be separated from the barcode sheet 137.

(5) The barcode label 137*d* is a detachable label to be attached to the delivery container together with the barcode label 137*b* and includes a barcode image corresponding to the delivery-container ID printed thereon.

<List of Data Output Source of Barcode Sheet>

FIG. 19 is a diagram illustrating a list of data output source of the barcode sheet according to the second embodiment of the present invention. The meaning of each item mentioned in the barcode sheet 137 is described.

A medical facility ID indicates a medical facility code managed by the medical facility M3.

The name of a medical facility indicates the name of a medical facility managed by the medical facility M3.

A scheduled administration date indicates an administration date managed by the drug status file F15.

A human-body ID indicates a human-body ID managed by the human-body management file F1.

A human-body ID barcode indicates a human-body ID managed by the human-body management file F1.

An administration management ID indicates an administration management ID managed by the administration management file F11.

A delivery-container ID for advance transportation of delivery container indicates a delivery-container ID managed by the administration management file F11.

A container identification barcode for advance transportation of delivery container indicates a delivery-container ID managed by the administration management file F11, an administration management ID managed by the administration management file F11, a drug ID managed by the administration management file F11, and a status (advance transportation).

A barcode for drug accommodation indicates a serial number (n) managed by the administration management file F11.

A delivery-container ID for delivery-container accommodation indicates a delivery-container ID managed by the administration management file F11.

A container identification barcode for delivery-container accommodation indicates a delivery-container ID managed by the administration management file F11, an administration management ID managed by the administration management file F11, a drug ID managed by the administration management file F11, and a status (collection).

<Barcode Label and Target to which Barcode Label is Attached>

FIG. 20 is a schematic diagram illustrating the barcode label according to the second embodiment of the present invention and a container to which the barcode label is attached.

The barcode labels 137*b* and 137*d* separated from the barcode sheet 137 by a staff of a culture facility are attached to a side surface of the delivery container 26.

Subsequently, the barcode label 137*c* separated from the barcode sheet 137 by the staff of the culture facility is attached to a side surface of the drug wrapping 140 in which a drug 141 is accommodated.

Further, the staff of the culture facility accommodates the drug wrapping 140 with the drug 141 accommodated therein in the drug package 139A.

<Procedure for Preventing Mix-Up of Drugs or the Like>

Figure 21:
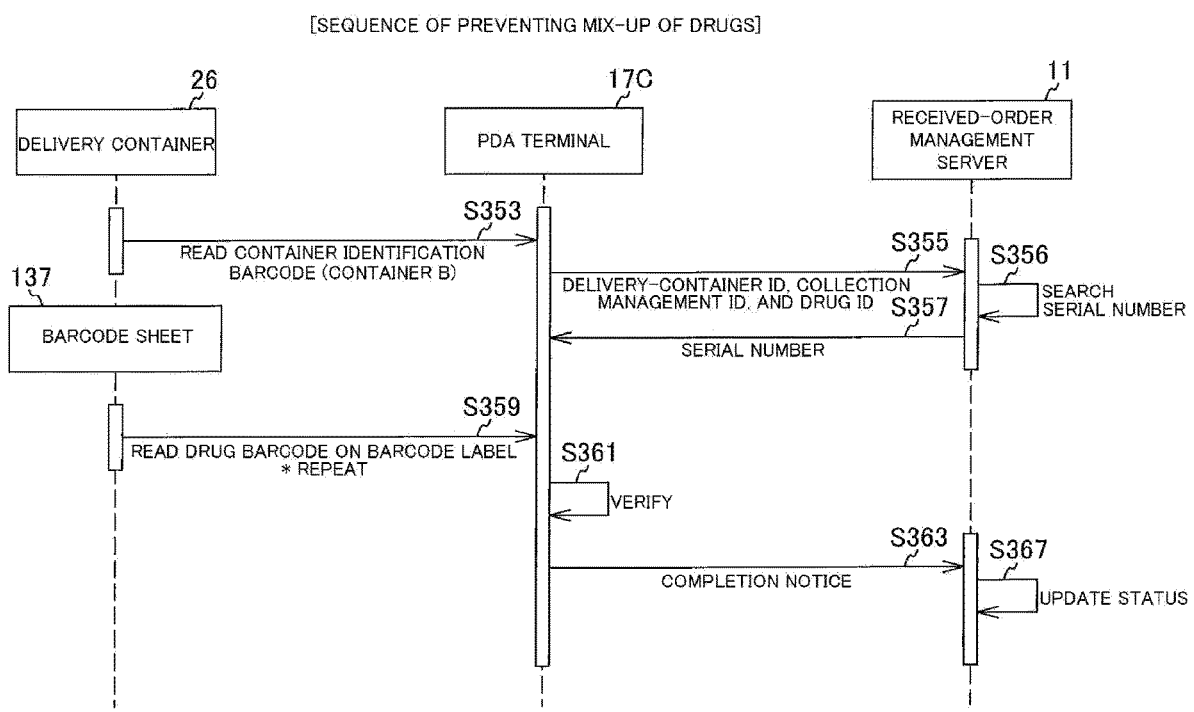
FIG. 21 is a sequence diagram illustrating a procedure for preventing an employee or a delivery person from accommodating a processed material in a container other than a specified container according to the second embodiment of the present invention.

FIG. 21 is a sequence diagram illustrating a procedure for preventing mix-up of drugs or the like in a culture facility according to the second embodiment of the present invention.

Here, a mix-up prevention procedure is described which is for preventing an employee or a delivery person from accommodating a processed material in a container other than a specified container in a culture facility.

At Step S353, a delivery person reads, from a barcode image on the barcode label 137*d* attached to the delivery container 26, its barcode information by using the barcode reader 17*f* provided in the PDA terminal 17C to acquire a delivery-container ID, a collection management ID, and a drug ID.

At Step S355, the PDA terminal 17C transmits the delivery-container ID, the collection management ID, and the drug ID read from the delivery container 26 to the received-order management server 11.

At Step S356, the received-order management server 11 performs search in the administration management file F11 by using the delivery-container ID, the collection management ID, and the drug ID received from the PDA terminal 17C as a key to acquire a serial number corresponding thereto.

At Step S357, the received-order management server 11 transmits the acquired serial number to the PDA terminal 17C.

At Step S359, the delivery person reads barcode information of each drug from a barcode image on the barcode sheet 137 by using the barcode reader 17*f* provided in the PDA terminal 17C to acquire each drug ID.

At Step S361, the PDA terminal 17C verifies whether the serial number acquired from the received-order management server 11 and each drug ID acquired from the barcode sheet 137 match each other to obtain a verification result (match/mismatch).

At Step S363, the PDA terminal 17C adds a completion notice to the verification result (match/mismatch) and transmits them to the received-order management server 11.

At Step S367, the received-order management server 11 updates the drug-delivery-container status file F13 and the drug status file F15 based on the verification result (match/mismatch) received from the PDA terminal 17C.

Third Embodiment

In a third embodiment, a modification of the collection process described in the first embodiment is described.

<Procedure of Advance Delivery of Barcode Sheet to Medical Facility>

Figure 22:
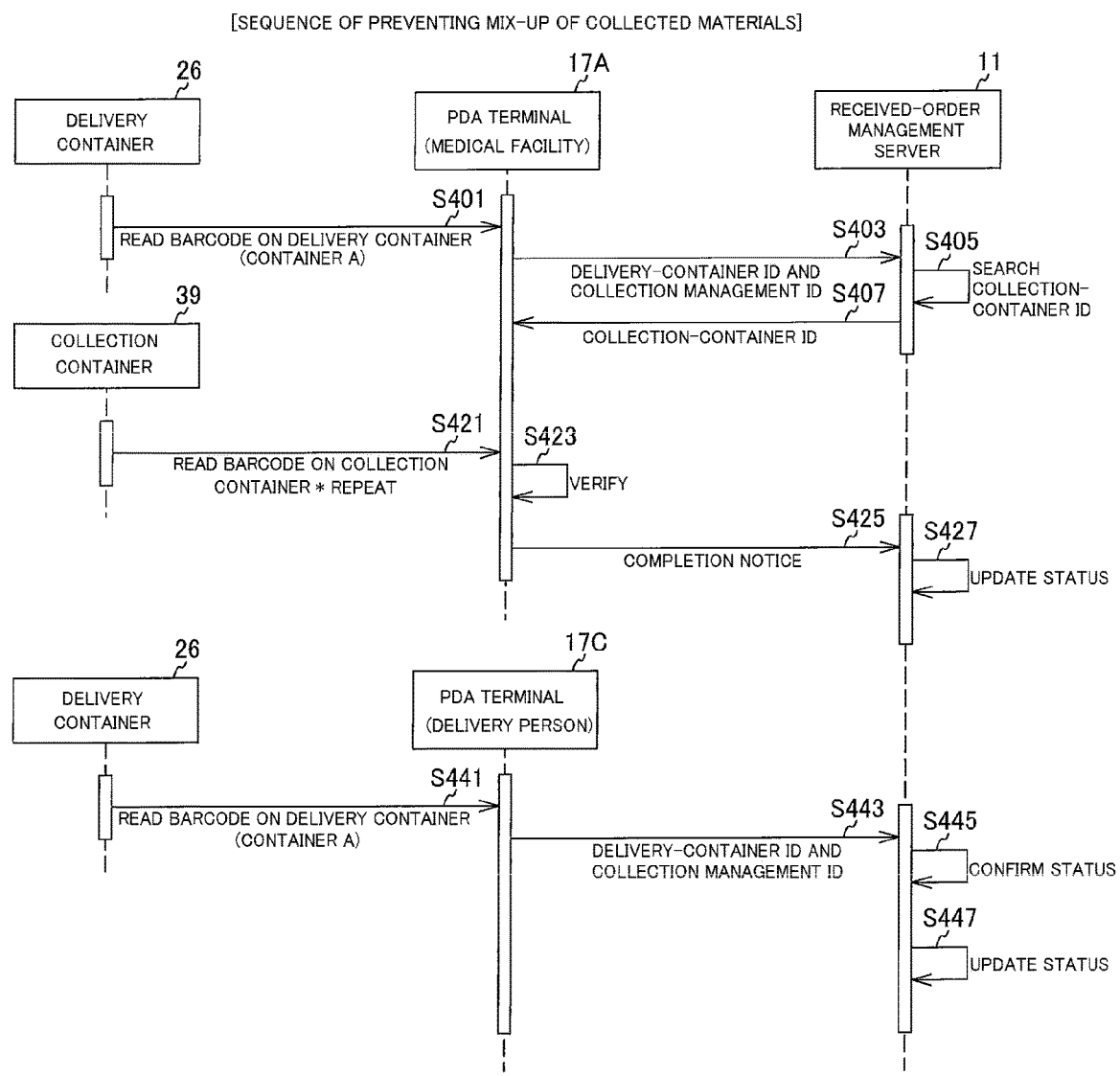
FIG. 22 is a sequence diagram illustrating a procedure of advance delivery of a printed barcode sheet to a medical facility, which is managed by a delivery management system according to a third embodiment of the present invention.

FIG. 22 is a sequence diagram illustrating a procedure of advance delivery of a printed barcode sheet to a medical facility, which is managed by a delivery management system according to the third embodiment of the present invention.

First, advance preparation is described before the procedure illustrated in FIG. 22 is described.

In a warehouse, a delivery person prepares a printed barcode sheet and the delivery container A and delivers them to a medical facility.

Next, in the medical facility, a medical staff accommodates a collected material (for example, bone marrow or blood) collected from a patient in the collection container 39. Next, the medical staff attaches a barcode label for collection container of the barcode sheet 37 to the collection container 39. Next, the medical staff attaches a barcode for delivery container of the barcode sheet 37 to the delivery container 26.

Next, the delivery person reads barcode information from a barcode image on the barcode label attached to the delivery container 26 by using the PDA terminal 17C.

The sequence diagram illustrated in FIG. 22 is described below.

At Step S401, the PDA terminal 17A carried by the medical staff of the medical facility reads barcode information from a barcode image on a barcode label attached to the delivery container 26 by using the barcode reader 17f. At this time, the medical staff accommodates the collection container 39 in the delivery container 26.

At Step S403, the PDA terminal 17A transmits the delivery-container ID and the collection management ID read from the delivery container 26 to the received-order management server 11.

At Step S405, the received-order management server 11 performs search in the administration management file F11 by using the delivery-container ID and the collection management ID received from the PDA terminal 17A as a key to acquire a collection-container ID corresponding thereto.

At Step S407, the received-order management server 11 transmits the acquired collection-container ID to the PDA terminal 17A.

At Step S421, the medical staff reads barcode information from a barcode image on the barcode label 37c attached to the collection container 39 by using the barcode reader 17f provided in the PDA terminal 17A to acquire a collection-container ID.

At Step S423, the PDA terminal 17A determines whether the collection-container ID acquired from the received-order management server 11 and each collection-container ID acquired from the barcode label 37c match each other to confirm consistency between them and obtain a verification result (match/mismatch).

At Step S425, the PDA terminal 17A adds a completion notice to the verification result (match/mismatch) and transmits them to the received-order management server 11.

At Step S427, the received-order management server 11 updates the status in the collection-container status file F7 and the status in the collected-material-delivery-container status F5 based on the verification result (match/mismatch) received from the PDA terminal 17A to indicate that a collection container has been accommodated.

In a warehouse of a delivery company, when receiving the delivery container 26, the delivery person reads the barcode information from the barcode image on the barcode label attached to the delivery container 26 to confirm that the status of the delivery container 26 indicates that the collection container has been accommodated.

At Step S441, the PDA terminal 17C carried by the delivery person reads the barcode information from the barcode image on the barcode label attached to the delivery container 26 by using the barcode reader 17f.

At Step S443, the PDA terminal 17C transmits the delivery-container ID and the collection management ID read from the delivery container 26 to the received-order management server 11.

At Step S445, the received-order management server 11 confirms that the status of the delivery container 26 indicates that the collection container has been accommodated.

At Step S447, the received-order management server 11 updates the status and a collection confirmation date and time in the collected-material-delivery-container status F5 based on the delivery-container ID and the collection management ID received from the PDA terminal 17C.

At Step S451, the received-order management server 11 transmits status information to the PDA terminal 17C.

<Procedure of Advance Delivery of Printed Barcode Sheet to Medical Facility>

Figure 23:
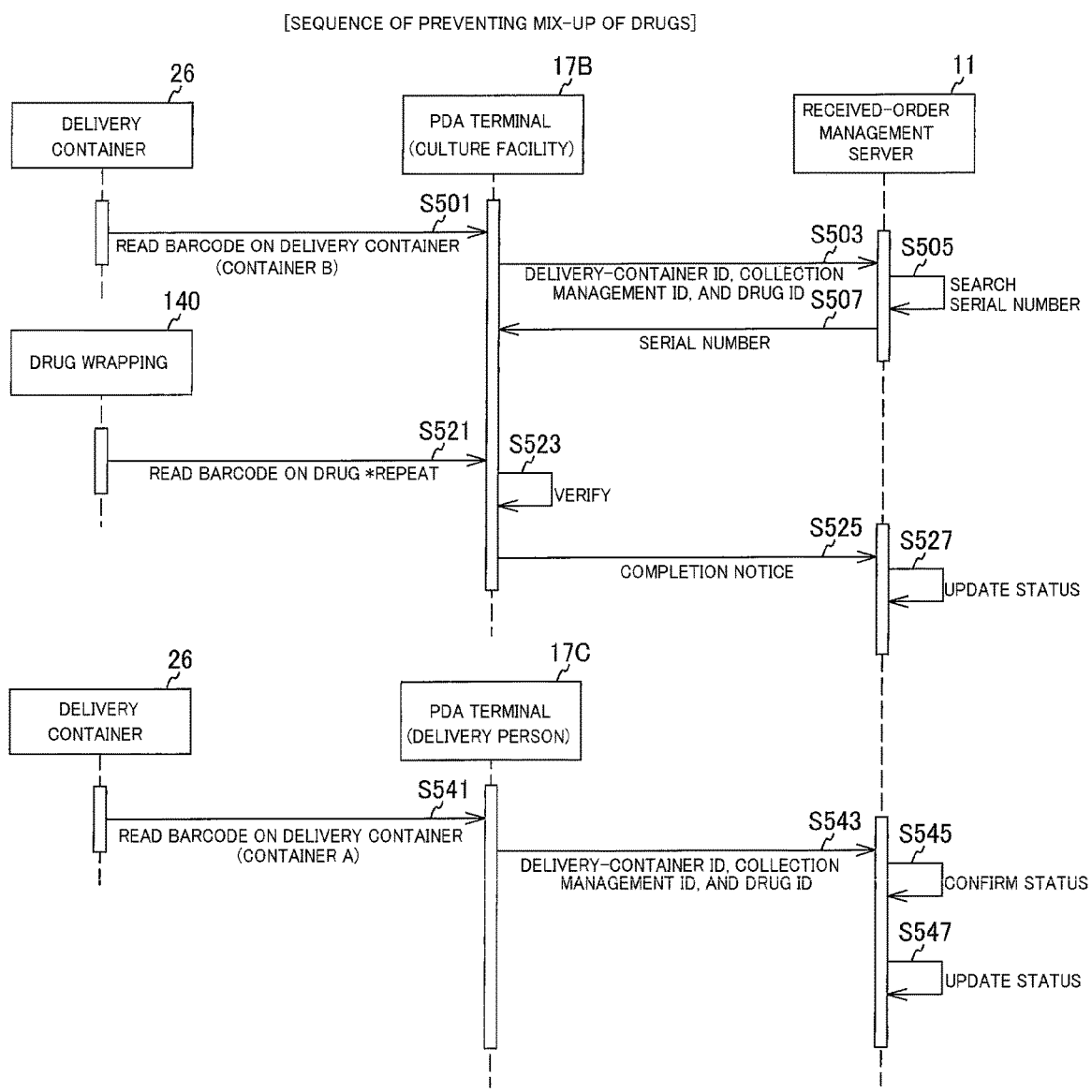
FIG. 23 is a sequence diagram illustrating a procedure of advance delivery of a printed barcode sheet to a medical facility, which is managed by the delivery management system according to the third embodiment of the present invention.

FIG. 23 is a sequence diagram illustrating a procedure of advance delivery of a printed barcode sheet to a medical facility, which is managed by the delivery management system according to the third embodiment of the present invention.

The sequence diagram illustrated in FIG. 23 is described below.

At Step S501, the PDA terminal 17A carried by a person involved in manufacturing in a culture facility reads barcode information from a barcode image on a barcode label attached to the delivery container 26 by using the barcode reader 17f.

At Step S503, the PDA terminal 17A transmits a delivery-container ID, a collection management ID, and a drug ID read from the delivery container 26 to the received-order management server 11.

At Step S505, the received-order management server 11 performs search in the administration management file F11 by using the delivery-container ID, the collection management ID, and the drug ID received from the PDA terminal 17A as a key to acquire a serial number corresponding thereto.

At Step S507, the received-order management server 11 transmits the acquired one or more serial numbers to the PDA terminal 17A.

At Step S521, the person involved in manufacturing in the culture facility reads barcode information from the barcode label 137c attached to the drug wrapping 140 by using the barcode reader 17f provided in the PDA terminal 17 to acquire a serial number of a drug.

At Step S523, the PDA terminal 17 verifies whether the serial number acquired from the received-order management server 11 and each serial number acquired from the barcode label 137c match each other to obtain a verification result (match/mismatch).

At Step S525, the PDA terminal 17 adds a completion notice to the verification result (match/mismatch) and transmits them to the received-order management server 11.

At Step S527, the received-order management server 11 updates the status in the drug status F and the status in the drug-delivery-container status F based on the verification result (match/mismatch) received from the PDA terminal 17 to indicate completion of accommodation.

In a warehouse of a delivery company, when receiving the delivery container 26, a delivery person reads barcode information from a barcode image on the barcode label attached to the delivery container 26 to confirm that the status of the delivery container 26 indicates that a collection container has been accommodated.

At Step S541, the PDA terminal 17C carried by the delivery person reads the barcode information from the barcode image on the barcode label attached to the delivery container 26 by using the barcode reader 17*f*.

At Step S543, the PDA terminal 17C transmits the delivery-container ID, the collection management ID, and the drug ID read from the delivery container 26 to the received-order management server 11.

At Step S545, the received-order management server 11 confirms that the status of the delivery container 26 indicates that a collection container has been accommodated therein.

At Step S547, the received-order management server 11 updates the status and a collection confirmation date and time in the drug-delivery-container status F based on the administration management ID, the delivery-container ID, and the drug ID received from the PDA terminal 17C.

Main Effects in the Above Embodiments

According to the above embodiments, it is possible to verify the drug wrapping (the article container) 140 by using the second barcode label 137*d* attached to a delivery container and the barcode-image portion 137*e* in a delivery destination. Therefore, it is possible to prevent mix-up of drug wrappings each including a drug accommodated therein without opening the delivery container. Further, it is possible to prevent mix-up of drugs.

The verification unit 17*s* can verify whether the first serial number received from the delivery management device 7 and the second serial number related to an article read from the barcode-image portion 137*e* on the barcode sheet 137 match each other. Therefore, it is possible to prevent mix-up of drug wrappings each including a drug accommodated therein without opening the delivery container. Further, it is possible to prevent mix-up of drugs.

At the delivery destination, the collection container 39 that is an article container can be verified by using the second barcode label 37*d* attached to the delivery container and the barcode-image portion 37*e*. Therefore, it is possible to prevent mix-up of collection containers each including a collected material accommodated therein without opening the delivery container. Further, it is possible to prevent mix-up of collected materials.

The verification unit 17*s* can verify whether the first serial number received from the delivery management device 7 and the second serial number related to an article read from the barcode-image portion 37*e* on the barcode sheet 37 match each other. Therefore, it is possible to prevent mix-up of collection containers each including a collected material accommodated therein without opening the delivery container. Further, mix-up of collected materials can be prevented.

Summary of Actions and Effects of Aspects in Present Embodiment

First Aspect

The delivery management system 1 according to the present aspect is characterized by including the drug wrapping (the article container) 140 that accommodates therein a drug as an article, the delivery container 26 for accommodating therein the drug wrapping (the article container) 140 and delivering it, the delivery management device 7 that generates barcode image data for specifying each of the drug wrapping (the article container) 140 and the delivery container 26, and the barcode sheet 137 on which a barcode image is printed based on the barcode image data generated by the delivery management device 7. The barcode sheet 137 includes the barcode label 137*c* (the first barcode label) indicating a serial number related to the drug as the article, the barcode-image portion 137*e* indicating the serial number related to the drug as the article, and the second barcode label 137*d* indicating a delivery-container ID related to the delivery container. When the drug wrapping (the article container) 140 to which the barcode label 137*c* (the first barcode label) separated from the barcode sheet 137 is attached, the delivery container 26, and the barcode sheet 137 from which the barcode label 137*c* (the first barcode label) has been separated reach a delivery destination, the drug wrapping (the article container) 140 is verified using the second barcode label 137*d* attached to the delivery container and the barcode-image portion 137*e* at the delivery destination.

According to the present aspect, it is possible to verify the drug wrapping (the article container) 140 using the second barcode label 137*d* attached to the delivery container and the barcode-image portion 137*e* at the delivery destination. Therefore, it is possible to prevent mix-up of drug wrappings each including a drug accommodated therein without opening the delivery container. Further, mix-up of drugs can be prevented.

Second Aspect

The delivery management system 1 according to the present aspect is characterized by including the PDA terminal 17C (the portable information terminal) that is carried by a delivery person of a delivery company of the delivery container and communicates with the delivery management device 7 via a communication network, the PDA terminal 17C (the portable information terminal) including the barcode reader 17*f* that reads barcode information from the barcode-image portion 137*e*, the first communication unit 17*t* that receives a first serial number related to an article from the delivery management device 7, and the verification unit 17*s* that verifies whether the first serial number received from the delivery management device 7 and a second serial number related to an article read from the barcode-image portion 137*e* on the barcode sheet 137 match each other.

According to the present aspect, the verification unit 17*s* can verify whether the first serial number received from the delivery management device 7 and the second serial number related to the article read from the barcode-image portion 137*e* on the barcode sheet 137 match each other. Therefore, it is possible to prevent mix-up of drug wrappings each including a drug accommodated therein without opening the delivery container. Further, mix-up of drugs can be prevented.

Third Aspect

The delivery management system 1 according to the present aspect is characterized in that an article container to which the first barcode label 37*c* separated from the barcode sheet 37 is attached, the delivery container 26 to which the second barcode label 37*d* separated from the barcode sheet 37 is attached, and the barcode sheet 37 from which those barcode labels have been separated are delivered to the delivery destination.

According to the present aspect, at the delivery destination, the collection container 39 that is an article container can be verified by using the second barcode label 37*d* attached to the delivery container and the barcode-image portion 37e. Therefore, it is possible to prevent mix-up of collection containers each including a collected material accommodated therein without opening the delivery container. Further, mix-up of collected materials can be prevented.

Fourth Aspect

The delivery management system 1 according to the present aspect is characterized by including the PDA terminal 17C (the portable information terminal) that is carried by a delivery person of a delivery company of the delivery container and communicates with the delivery management device 7 via a communication network, the PDA terminal 17C (the portable information terminal) including the barcode reader 17f that reads barcode information from a barcode image, the first communication unit 17t that transmits a delivery-container ID read from the barcode label 37c attached to the delivery container 26 to the delivery management device 7 and receives a first serial number related to an article corresponding to that delivery-container ID from the delivery management device 7, and the verification unit 17s that verifies whether the first serial number received from the delivery management device 7 and a second serial number related to an article read from the barcode-image portion 37e on the barcode sheet 37 match each other.

According to the present aspect, the verification unit 17s can verify whether the first serial number received from the delivery management device 7 and the second serial number related to the article read from the barcode-image portion 37e on the barcode sheet 37 match each other. Therefore, it is possible to prevent mix-up of collection containers each including a collected material accommodated therein without opening the delivery container. Further, mix-up of collected materials can be prevented.

Fifth Aspect

The delivery management system 1 according to the present aspect is characterized by including the PDA terminal 17C (the portable information terminal) that is carried by a delivery person of a delivery company of the delivery container and communicates with the delivery management device 7 via a communication network, the PDA terminal 17C (the portable information terminal) including the barcode reader 17f that reads barcode information from a barcode image, the first communication unit 17t that transmits a delivery-container ID read from a barcode label attached to the delivery container 26 to the delivery management device 7 and receives a first serial number related to an article corresponding to that delivery-container ID from the delivery management device 7, and the verification unit 17s that verifies whether the first serial number received from the delivery management device 7 and a second serial number related to an article container read from the barcode-image portion 37e on the barcode sheet 37 match each other.

According to the present aspect, the verification unit 17s can verify whether the first serial number received from the delivery management device 7 and the second serial number related to the article container read from the barcode-image portion 37e on the barcode sheet 37 match each other. Therefore, it is possible to prevent mix-up of collection containers each including a collected material accommodated therein without opening the delivery container. Further, mix-up of collected materials can be prevented.

Sixth Aspect

The first barcode label 137c according to the present aspect is characterized by being attached to the drug wrapping 140 (or a collected-material wrapping) in which a collected material or a drug is accommodated.

According to the present aspect, the first barcode label 137c is attached to the drug wrapping 140 (or the collected-material package) that accommodates therein a collected material or a drug. Therefore, although a verification operation is performed while the drug wrapping 140 (or the collected-material package) is accommodated in the delivery container, it is possible to prevent mix-up of drug wrappings each including the collected material or the drug accommodated therein without opening the delivery container. Further, it is possible to prevent mix-up of drugs.

Seventh Aspect

The delivery management system 1 according to the present aspect is characterized by including the PDA terminal 17 that is carried by a medical staff who collects the article or a person involved in manufacturing in a culture facility processing the article and that communicates with the delivery management device 7 via a communication network, the PDA terminal 17 including the barcode reader 17f that reads barcode information from a barcode image, the first communication unit 17t that transmits a delivery-container ID read from a barcode label attached to the delivery container to the delivery management device 7 and receives a first article identification number corresponding to that delivery-container ID from the delivery management device 7, and the verification unit 17s that verifies whether the first article identification number received from the delivery management device 7 and a second article identification number related to an article container read from the article container match each other.

According to the present aspect, the verification unit 17s can verify whether the first article identification number received from the delivery management device 7 and the second article identification number related to the article container read from the article container match each other. Therefore, mix-up of article containers can be prevented.

Eighth Aspect

The delivery management system 1 according to the present aspect is characterized in that the first barcode label 137c and the barcode-image portion 137e provided on the barcode sheet each have one identical barcode image indicating an article identification number related to a drug and are printed on the barcode sheet 137 for the number of drugs.

According to the present aspect, the first barcode label 137c and the barcode-image portion 137e provided on the barcode sheet each have one identical barcode image indicating the article identification number related to the drug and are printed on the barcode sheet 137 for the number of drugs. Therefore, it is possible to perform identification for the number of drugs, and it is possible to prevent mix-up of drug containers each including a drug accommodated therein without opening the delivery container. Further, mix-up of drugs can be prevented.

Ninth Aspect

The delivery management system 1 according to the present aspect is characterized in that the first barcode label 37c and the barcode-image portion 37e provided on the barcode sheet each have one identical barcode image indicating an article identification number related to the collected material and are printed on the barcode sheet 37 for the number of collected materials.

According to the present aspect, the first barcode label 37c and the barcode-image portion 37e provided on the barcode sheet each have one identical barcode image indicating the article identification number related to the collected material and are printed on the barcode sheet 37 for the number of collected materials. Therefore, it is possible to perform identification for the number of collected materials, and it is possible to prevent mix-up of collection containers each including a collected material accommodated therein without opening the delivery container. Further, mix-up of collected materials can be prevented.

Tenth Aspect

The first barcode label 37c according to the present aspect is characterized by being printed for the number of the collected materials or the drugs on the barcode sheet 37.

According to the present aspect, the first barcode label 37c is printed on the barcode sheet 37 for the number of collected materials or drugs. Therefore, it is possible to perform identification for the number of collected materials, and it is possible to prevent mix-up of collection containers each including a collected material accommodated therein without opening the delivery container. Further, mix-up of collected materials can be prevented.

Eleventh Aspect

The first barcode label 37c according to the present aspect is characterized by being attached to the collection container 39 that is an article container.

According to the present aspect, it is possible to confirm the number of collection containers 39 accommodated in the delivery container 26 without opening the lid 26a of the delivery container 26 by visually confirming the number of blank areas each generated by detaching the barcode label from the barcode sheet 37, as described in the first embodiment.

Meanwhile, the first barcode label 137c according to the present aspect is characterized by being attached to the drug wrapping 140 that is an article container.

According to the present aspect, it is possible to perform a verification process by reading the barcode label 137c attached to the drug wrapping 140 by using the PDA terminal 17c when the drug wrapping 140 is accommodated in the delivery container 26, as described in the second embodiment. Therefore, mix-up of drugs can be prevented.

Twelfth Aspect

The delivery management device 7 according to the present aspect is characterized by including the barcode-information generation unit 7c that generates a barcode image indicating an article identification number related to the article container, a barcode image indicating a delivery-container ID related to the delivery container 26, and a barcode image indicating a serial number related to the article.

According to the present aspect, the barcode-information generation unit 7c generates the barcode image indicating the article identification number related to the article container, the barcode image indicating the delivery-container ID related to the delivery container 26, and the barcode image indicating the serial number related to the article. Therefore, it is possible to prevent mix-up of article containers each including an article accommodated therein without opening the delivery container. Further, mix-up of articles can be prevented.

Thirteenth Aspect

The delivery management device 7 according to the present aspect is characterized by including the database DB15 that memorizes a serial number related to an article to be accommodated in the article container and a delivery-container ID related to the delivery container 26 in association with each other, the second communication unit 7a that receives a delivery-container ID read from a barcode label attached to the delivery container 26 from the portable information terminal, and the search unit 7d that searches a serial number in the database DB15 by using the received delivery-container ID as a key, the second communication unit 7a transmitting the serial number acquired from the database DB15 to the PDA terminal 17C (the portable information terminal).

According to the present aspect, the second communication unit 7a can perform verification using the serial number related to the article accommodated in the article container in the PDA terminal 17C (the portable information terminal) by transmitting the serial number acquired from the database DB15 to the PDA terminal 17C (the portable information terminal).

Fourteenth Aspect

The delivery management device 7 according to the present aspect is characterized by including the database DB15 that memorizes an article identification number related to an article container and a delivery-container ID related to the delivery container 26 in association with each other, the second communication unit 7a that receives a delivery-container ID read from the barcode label 37d attached to the delivery container 26 from the PDA terminal 17C (the portable information terminal), and the search unit 7d that searches an article identification number in the database DB15 by using the received delivery-container ID as a key, the second communication unit 7a transmitting the article identification number acquired from the database DB15 to the PDA terminal 17C (the portable information terminal).

According to the present aspect, the second communication unit 7a can perform verification using the article identification number in the PDA terminal 17C (the portable information terminal) by transmitting the article identification number acquired from the database DB15 to the PDA terminal 17C (the portable information terminal).

Fifteenth Aspect

The delivery management system 1 according to the present aspect is characterized by including the warehouse terminal 21 that receives a shipping instruction from the delivery management device 7 and transmits a request for generating a barcode image to the delivery management device 7 in response to the shipping instruction, the warehouse terminal 21 printing the barcode image received from the barcode-information generation unit 7c of the delivery management device 7 on the barcode sheet 37.

According to the present aspect, the warehouse terminal 21 prints the barcode image received from the barcode-information generation unit 7c of the delivery management device 7 on the barcode sheet 37. Therefore, it is possible to print the barcode sheet 37 by using the warehouse terminal 21.

Sixteenth Aspect

The verification unit 17s according to the present aspect is characterized by transmitting the verification result obtained by verification to the delivery management device 7.

According to the present aspect, the verification unit 17s can register the verification result obtained by the verification in the delivery management device 7 by transmitting the verification result to the delivery management device 7.

Seventeenth Aspect

The delivery management system 1 according to the present aspect is characterized by including the delivery vehicle 25 that delivers the delivery container 26, wherein the delivery vehicle 25 performs delivery for the regenerative medicine process K1 related to autologous cells including the first delivery process K3 and the second delivery process K5, delivers the delivery container 26 with the collected material placed thereon from a medical facility to a culture facility as the first delivery process K3, and delivers the delivery container 26 with the drug placed thereon from the culture facility to the medical facility as the second delivery process K5.

According to the present aspect, it is possible to prevent mix-up of a plurality of different kinds of delivered articles and to automate a verification process for a regenerative medicine process.

REFERENCE SIGNS LIST 1 delivery management system, 3, 4, 5 client terminal, 7 delivery management device, 7a communication unit, 7b communication unit, 7c barcode-information generation unit, 7d search unit, 7s controller, 9 front-end server, 11 received-order management server, 13 logistics management server, 17, 17A, 17B, 17C PDA terminal, 17d operation display unit, 17e GPS receiver, 17f barcode reader, 17g wireless communication unit, 17s verification unit, 17t communication unit, 19, 19A, 19B, 19C printer, 19a wireless communication unit, 19b memory medium, 21 warehouse terminal, 21a main controller, 21b CPU, 21c ROM, 21d RAM, 21e timer, 21f display controller, 21g display unit, 21h communication unit, 21i operation unit, 21j wireless communication unit, 23 printer, 23a wireless communication unit, 25 delivery vehicle, 26 delivery container, 26A, 26B article container, 27 small terminal, 27a communication unit, 27b CPU, 27c RAM, 27d ROM, 27e GPS receiver, 27f operation display unit, 27g axis sensor, 27h bus, 31 medical facility, 35 culture facility, 37 barcode sheet, 37a, 37b, 37c, 37d barcode label, 37e barcode-image portion, 39 collection container, 137, 137a barcode label, 137a, 137b, 137c, 137d barcode label, 137b barcode label, 137e barcode-image portion, 139A drug package, 140 drug wrapping, 141 drug, N1, N2, N3 communication network.

The invention claimed is:
1. A delivery management system comprising:
an article container for accommodating therein an article;
a delivery container for accommodating therein the article container and delivering the article container;
a delivery management device that generates barcode image data specifying each of the article container and the delivery container; and
a barcode sheet on which a barcode image is printed based on the barcode image data generated by the delivery management device, and
a portable information terminal that is carried by a delivery person of a delivery company of the delivery container and communicates with the delivery management device via a communication network, wherein
the barcode sheet includes
a first barcode label indicating an article identification number related to the article,
a barcode-image portion indicating the article identification number related to the article, and
a second barcode label indicating a delivery-container identification ID related to the delivery container, and
when an article container to which the first barcode label separated from the barcode sheet is attached, the delivery container, and the barcode sheet from which the first barcode label has been separated reach a delivery destination, the article container is verified using the second barcode label attached to the delivery container and the barcode-image portion at the delivery destination,
the portable information terminal includes
a barcode reader that reads barcode information from a barcode image,
a first communication unit that receives a first article identification number related to an article from the delivery management device, and
a verification unit that verifies whether the first article identification number received from the delivery management device and a second article identification number related to an article read from the barcode-image portion on the barcode sheet match each other.
2. The delivery management system according to claim 1, wherein the verification unit transmits a result of the verification to the delivery management device.
3. A delivery management system comprising:
an article container for accommodating therein an article;
a delivery container for accommodating therein the article container and delivering the article container;
a delivery management device that generates barcode image data specifying each of the article container and the delivery container; and
a barcode sheet on which a barcode image is printed based on the barcode image data generated by the delivery management device, and
a portable information terminal that is carried by a delivery person of a delivery company of the delivery container and communicates with the delivery management device via a communication network, wherein
the barcode sheet includes
a first barcode label indicating an article identification number related to the article,
a barcode-image portion indicating the article identification number related to the article, and
a second barcode label indicating a delivery-container identification ID related to the delivery container,
when an article container to which the first barcode label separated from the barcode sheet is attached, the delivery container, and the barcode sheet from which the first barcode label has been separated reach a delivery destination, the article container is verified using the second barcode label attached to the delivery container and the barcode-image portion at the delivery destination, and an article container to which the first barcode label separated from the barcode sheet is attached, a delivery container to which the second barcode label separated from the barcode sheet is attached, and the barcode sheet from which the barcode labels have been separated are delivered to a delivery destination, the portable information terminal includes a barcode reader that reads barcode information from a barcode image, a first communication unit that transmits a delivery-container identification ID read from a barcode label attached to the delivery container to the delivery management device and receives a first article identification number related to an article corresponding to the delivery-container identification ID from the delivery management device, and a verification unit that verifies whether the first article identification number received from the delivery management device and a second article identification number related to an article read from the barcode-image portion on the barcode sheet match each other.

4. The delivery management system according to claim 3, further comprising a portable information terminal that is carried by a medical staff who collects the article or a person involved in manufacturing in a culture facility processing the article and that communicates with the delivery management device via a communication network, wherein the portable information terminal includes a barcode reader that reads barcode information from a barcode image, a first communication unit that transmits the delivery-container identification ID read from a barcode label attached to the delivery container to the delivery management device and receives a first article identification number corresponding to the delivery-container identification ID from the delivery management device, and a verification unit that verifies whether the first article identification number received from the delivery management device and a second article identification number related to an article container read from the article container match each other.

5. A delivery management system comprising:

an article container for accommodating therein an article;

a delivery container for accommodating therein the article container and delivering the article container;

a delivery management device that generates barcode image data specifying each of the article container and the delivery container; and a barcode sheet on which a barcode image is printed based on the barcode image data generated by the delivery management device, wherein the barcode sheet includes a first barcode label indicating an article identification number related to the article, a barcode-image portion indicating the article identification number related to the article, and a second barcode label indicating a delivery-container identification ID related to the delivery container, and when an article container to which the first barcode label separated from the barcode sheet is attached, the delivery container, and the barcode sheet from which the first barcode label has been separated reach a delivery destination, the article container is verified using the second barcode label attached to the delivery container and the barcode-image portion at the delivery destination, wherein the first barcode label is attached to a wrapping in which a collected material or a drug is accommodated, wherein the delivery management device includes a database that memorizes an article identification number related to the article container and a delivery-container identification ID related to the delivery container in association with each other, a second communication unit that receives a delivery-container identification ID read from a barcode label attached to the delivery container from a portable information terminal, and a search unit that searches an article identification number in the database by using the received delivery-container identification ID as a key, wherein the second communication unit transmits the article identification number acquired from the database to the portable information terminal.

6. The delivery management system according to claim 5, further comprising a warehouse terminal that receives a shipping instruction from the delivery management device and transmits a request for generating a barcode image to the delivery management device in response to the shipping instruction, wherein the warehouse terminal prints the barcode image received from the delivery management device on the barcode sheet.

7. A delivery management system comprising:

an article container for accommodating therein an article;

a delivery container for accommodating therein the article container and delivering the article container;

a delivery management device that generates barcode image data specifying each of the article container and the delivery container; and a barcode sheet on which a barcode image is printed based on the barcode image data generated by the delivery management device, and a delivery vehicle that delivers the delivery container, wherein the barcode sheet includes a first barcode label indicating an article identification number related to the article, a barcode-image portion indicating the article identification number related to the article, and a second barcode label indicating a delivery-container identification ID related to the delivery container, and when an article container to which the first barcode label separated from the barcode sheet is attached, the delivery container, and the barcode sheet from which the first barcode label has been separated reach a delivery destination, the article container is verified using the second barcode label attached to the delivery container and the barcode-image portion at the delivery destination, the delivery vehicle performs delivery for a regenerative medicine process related to autologous cells including a first delivery process and a second delivery process, delivers the delivery container with a collected material placed thereon from a medical facility to a culture facility as the first delivery process, and delivers the delivery container with a drug placed thereon from the culture facility to the medical facility as the second delivery process.

* * * * *